US010372878B2

(12) United States Patent
Van Arkel et al.

(10) Patent No.: US 10,372,878 B2
(45) Date of Patent: Aug. 6, 2019

(54) SECURE COMMUNICATIONS

(71) Applicant: Verizon Patent and Licensing Inc., Arlington, VA (US)

(72) Inventors: John H. Van Arkel, Colorado Springs, CO (US); James J. Wagner, Colorado Springs, CO (US); Corrine L. Schweyen, Columbus, OH (US); Saralyn M. Mahone, Colorado Springs, CO (US); David D. Tada, Colorado Springs, CO (US); Terrill J. Curtis, Pueblo West, CO (US); Scott Hagins, Colorado Springs, CO (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 616 days.

(21) Appl. No.: 14/837,950

(22) Filed: Aug. 27, 2015

(65) Prior Publication Data

US 2015/0363557 A1 Dec. 17, 2015

Related U.S. Application Data

(63) Continuation-in-part of application No. 13/536,460, filed on Jun. 28, 2012, now abandoned.
(Continued)

(51) Int. Cl.
*G16H 10/60* (2018.01)
*G06F 19/00* (2018.01)
*G06Q 10/10* (2012.01)

(52) U.S. Cl.
CPC .......... *G06F 19/328* (2013.01); *G06Q 10/10* (2013.01)

(58) Field of Classification Search
CPC .............................. G06F 19/328; G16H 10/60
See application file for complete search history.

(56) References Cited

U.S. PATENT DOCUMENTS

2003/0061212 A1* 3/2003 Smith .................... G06Q 10/06
2003/0115195 A1 6/2003 Fogel et al.
(Continued)

OTHER PUBLICATIONS

Liles et al., "Predictive Modeling in Medical Billing: The Latest Advance id Sophisticated Data Mining Techniques are Enabling ZPICs and Law Enforcement to Identify Fraud Sooner and Prevent it from Continuing" Apr. 19, 2011, 3 pages.
(Continued)

*Primary Examiner* — John A Pauls

(57) ABSTRACT

A system for providing secure communications may include a management system to receive first information, the first information being received via a first secure connection, analyze the received information to form analyzed information, and provide the analyzed information, a processor device to receive the analyzed information, the analyzed information being received via a second secure connection between the processor device and the management system, and perform an action based on the analyzed information, and a clearinghouse device to receive second information, the second information being received via a third secure connection between the clearinghouse device and each provider device of a plurality of provider devices, process the second information to form the first information, and provide the first information to the management system via the first secure connection.

20 Claims, 19 Drawing Sheets

Related U.S. Application Data

(60) Provisional application No. 61/503,339, filed on Jun. 30, 2011.

(56) References Cited

U.S. PATENT DOCUMENTS

2003/0229519 A1* 12/2003 Eidex .................... G06F 19/328 705/2
2005/0276401 A1 12/2005 Madill et al.
2007/0011032 A1* 1/2007 Bregante ............... G06F 19/328 705/4
2008/0249820 A1 10/2008 Pathria et al.
2009/0094064 A1* 4/2009 Tyler ..................... G06F 19/328 705/4
2009/0099884 A1* 4/2009 Hoefelmeyer ..... G06Q 10/0639 705/7.38
2009/0254379 A1 10/2009 Adams et al.
2012/0215553 A1* 8/2012 Leston ................... G06Q 10/10 705/2
2016/0162165 A1* 6/2016 Lingappa .............. G06T 11/206 715/771

OTHER PUBLICATIONS

Medicare Program Integrity Manual Chapter 1—Medicare Improper Payments: Measuring, Correcting, and Preventing Overpayments and Underpayments, CMS, Nov. 20, 2009, 14 pages.
Medicare Program Integrity Manual Chapter 2—Data Analysis, CMS, Nov. 20, 2009, 10 pages.
Medicare Program Integrity Manual Chapter 4—Benefit Integrity, CMS, Nov. 20, 2009, 177 pages.

* cited by examiner

520

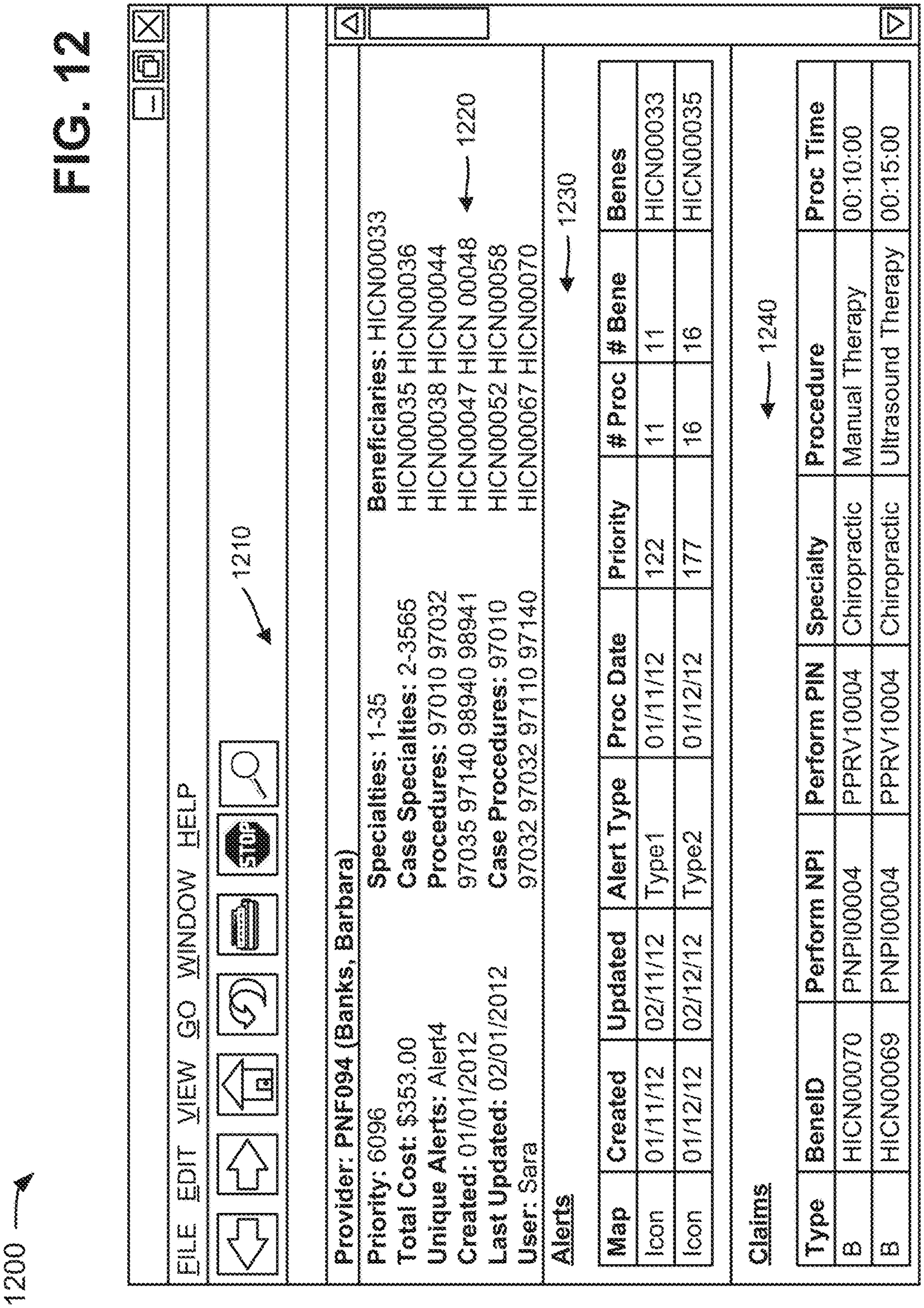

FIG. 12

FILE  EDIT  VIEW  GO  WINDOW  HELP

── 1210

Provider: PNF094 (Banks, Barbara)

| Priority: 6096 | Specialties: 1-35 | Beneficiaries: HICN00033 |
| Total Cost: $353.00 | Case Specialties: 2-3565 | HICN00035 HICN00036 |
| Unique Alerts: Alert4 | Procedures: 97010 97032 | HICN00038 HICN00044 |
| Created: 01/01/2012 | 97035 97140 98940 98941 | HICN00047 HICN 00048 ── 1220 |
| Last Updated: 02/01/2012 | Case Procedures: 97010 | HICN00052 HICN00058 |
| User: Sara | 97032 97110 97140 | HICN00067 HICN00070 |

Alerts ── 1230

| Map | Created | Updated | Alert Type | Proc Date | Priority | # Proc | # Bene | Benes |
|---|---|---|---|---|---|---|---|---|
| Icon | 01/11/12 | 02/11/12 | Type1 | 01/11/12 | 122 | 11 | 11 | HICN00033 |
| Icon | 01/12/12 | 02/12/12 | Type2 | 01/12/12 | 177 | 16 | 16 | HICN00035 |

Claims ── 1240

| Type | BeneID | Perform NPI | Perform PIN | Specialty | Procedure | Proc Time |
|---|---|---|---|---|---|---|
| B | HICN00070 | PNPI00004 | PPRV10004 | Chiropractic | Manual Therapy | 00:10:00 |
| B | HICN00069 | PNPI00004 | PPRV10004 | Chiropractic | Ultrasound Therapy | 00:15:00 |

1200

SECURE COMMUNICATIONS

RELATED APPLICATION

This application is a continuation-in-part of U.S. patent application Ser. No. 13/536,460, filed Jun. 28, 2012, which claims priority under 35 U.S.C. § 119 based on U.S. Provisional Patent Application No. 61/503,339, filed Jun. 30, 2011, the disclosures of which are incorporated by reference herein in their entireties.

BACKGROUND

Healthcare fraud is a sizeable and significant challenge for the healthcare and insurance industries, and costs these industries billions of dollars each year. Healthcare fraud is a significant threat to most healthcare programs, such as government sponsored programs and private programs. Currently, healthcare providers, such as doctors, pharmacies, hospitals, etc., provide healthcare services to beneficiaries, and submit healthcare claims for the provision of such services. The healthcare claims are provided to a clearinghouse that makes minor edits to the claims, and provides the edited claims to a claims processor. The claims processor, in turn, processes, edits, and/or pays the healthcare claims. The clearinghouse and/or the claims processor may be associated with one or more private or public health insurers and/or other healthcare entities.

After paying the healthcare claims, the claims processor forwards the paid claims to a zone program integrity contractor. The zone program integrity contractor reviews the paid claims to determine whether any of the paid claims are fraudulent. A recovery audit contractor may also review the paid claims to determine whether any of them are fraudulent. In one example, the paid claims may be reviewed against a black list of suspect healthcare providers. If the zone program integrity contractor or the recovery audit contractor discovers a fraudulent healthcare claim, they may attempt to recover the monies paid for the fraudulent healthcare claim. However, such after-the-fact recovery methods (e.g., pay and chase methods) are typically unsuccessful since an entity committing the fraud may be difficult to locate due to the fact that the entity may not be a legitimate person, organization, business, etc. Furthermore, relying on law enforcement agencies to track down and prosecute such fraudulent entities may prove fruitless since law enforcement agencies lack the resources to handle healthcare fraud and it may require a long period of time to build a case against the fraudulent entities.

BRIEF DESCRIPTION OF THE DRAWINGS

FIG. 12 is a diagram of an example user interface, for a particular entity, that may be generated or provided by the healthcare fraud management system;

DETAILED DESCRIPTION OF PREFERRED EMBODIMENTS

The following detailed description refers to the accompanying drawings. The same reference numbers in different drawings may identify the same or similar elements.

An implementation, described herein, may detect a fraudulent healthcare claim, from a provider, by providing healthcare fraud detection tools and claims review processes in a near real-time pre-payment model and by rapidly adapting the fraud detection tools and practices as an environment changes. In one implementation, when a healthcare claim is determined to be fraudulent, the claim may be denied or challenged prior to payment by a claims processor. Alternatively, or additionally, healthcare claims associated with a particular entity may be received, and rules may be selected for the healthcare claims based on the types of claims. The healthcare claims may be processed using the selected rules, and alarms, generated by the processed healthcare claims, may be collected and sorted. Healthcare information associated with the particular entity may be prioritized in relation to healthcare information associated with other entities, based on the collected and sorted alarms. The prioritized healthcare information associated with the particular entity and the other entities may be provided for display. When selection of the healthcare information associated with the particular entity is received, information associated with healthcare claims of the particular entity may be provided for display.

Figure 1:
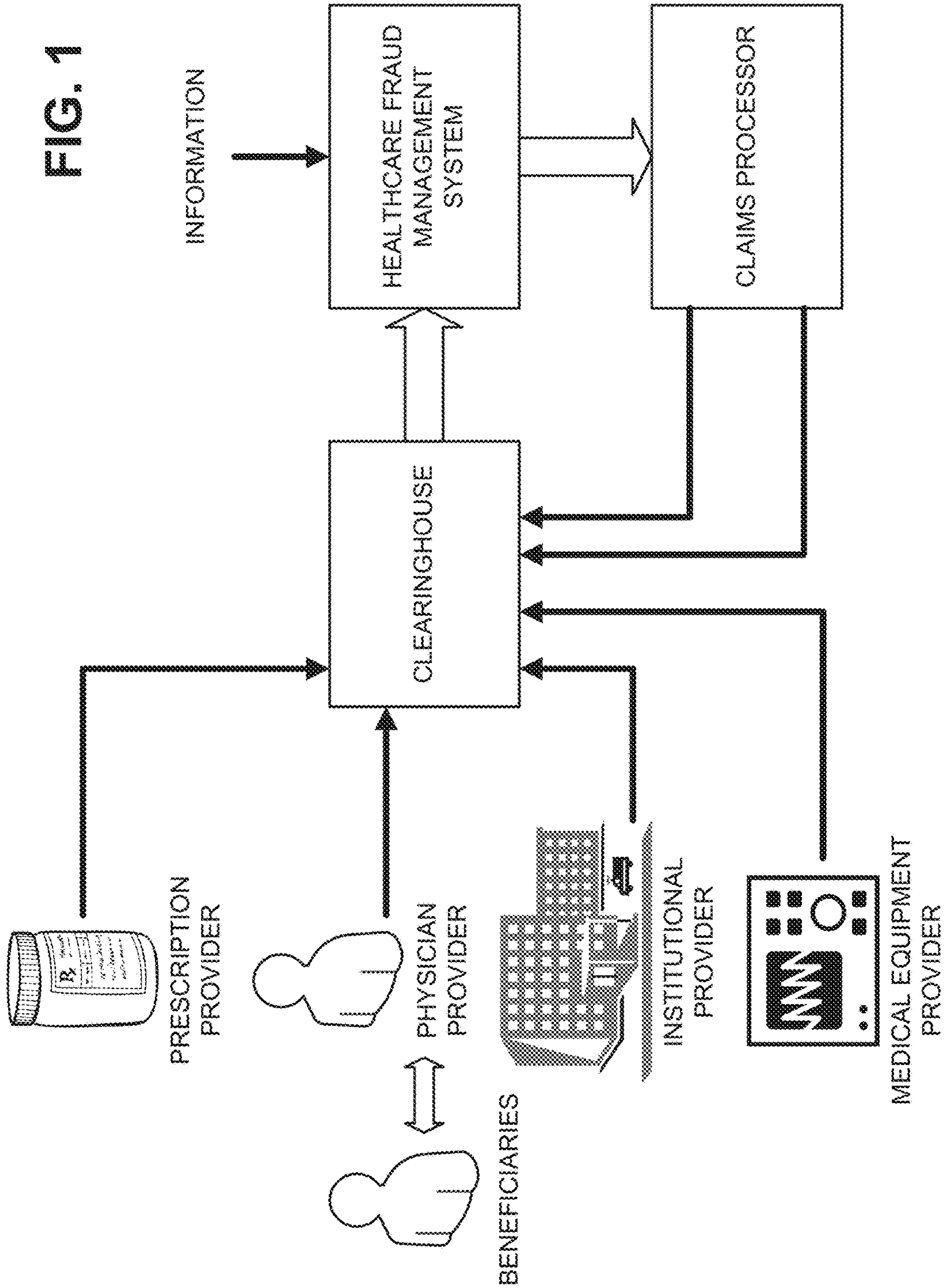
FIG. 1 is a diagram of an overview of an implementation described herein.

FIG. 1 is a diagram of an overview of an implementation described herein. For the example of FIG. 1, assume that beneficiaries receive healthcare services from a provider, such as a prescription provider, a physician provider, an institutional provider, a medical equipment provider, etc. The term "beneficiary," as used herein, is intended to be broadly interpreted to include a member, a person, a business, an organization, or some other type of entity that receives healthcare services, such as prescription drugs, surgical procedures, doctor's office visits, physicals, hospital care, medical equipment, etc. from a provider. The term "provider," as used herein, is intended to be broadly interpreted to include a prescription provider (e.g., a drug store, a pharmaceutical company, an online pharmacy, a brick and mortar pharmacy, etc.), a physician provider (e.g., a doctor, a surgeon, a physical therapist, a nurse, a nurse assistant, etc.), an institutional provider (e.g., a hospital, a medical emergency center, a surgery center, a trauma center, a clinic, etc.), a medical equipment provider (e.g., diagnostic equipment provider, a therapeutic equipment provider, a life support equipment provider, a medical monitor provider, a medical laboratory equipment provider, a home health agency, etc.), etc.

After providing the healthcare services, the provider may submit claims to a clearinghouse. The terms "claim" or "healthcare claim," as used herein, are intended to be broadly interpreted to include an interaction of a provider with a clearinghouse, a claims processor, or another entity responsible for paying for a beneficiary's healthcare or medical expenses, or a portion thereof. The interaction may involve the payment of money, a promise for a future payment of money, the deposit of money into an account, or the removal of money from an account. The term "money," as used herein, is intended to be broadly interpreted to include anything that can be accepted as payment for goods or services, such as currency, coupons, credit cards, debit cards, gift cards, and funds held in a financial account (e.g., a checking account, a money market account, a savings account, a stock account, a mutual fund account, a paypal account, etc.). The clearinghouse may make minor changes to the claims, and may provide information associated with the claims, such as provider information, beneficiary information, healthcare service information, etc., to a healthcare fraud management system.

In one implementation, each healthcare claim may involve a one time exchange of information, between the clearinghouse and the healthcare fraud management system, which may occur in near real-time to submission of the claim to the clearinghouse and prior to payment of the claim. Alternatively, or additionally, each healthcare claim may involve a series of exchanges of information, between the clearinghouse and the healthcare fraud management system, which may occur prior to payment of the claim.

The healthcare fraud management system may receive the claims information from the clearinghouse and may obtain other information regarding healthcare fraud from other systems. For example, the other healthcare fraud information may include information associated with providers under investigation for possible fraudulent activities, information associated with providers who previously committed fraud, information provided by zone program integrity contractors (ZPICs), information provided by recovery audit contractors, etc. The information provided by the zone program integrity contractors may include cross-billing and relationships among healthcare providers, fraudulent activities between Medicare and Medicaid claims, whether two insurers are paying for the same services, amounts of services that providers bill, etc. The recovery audit contractors may provide information about providers whose billings for services are higher than the majority of providers in a community, information regarding whether beneficiaries received healthcare services and whether the services were medically necessary, information about suspended providers, information about providers that order a high number of certain items or services, information regarding high risk beneficiaries, etc. The healthcare fraud management system may use the claims information and the other information to facilitate the processing of a particular claim. In one example implementation, the healthcare fraud management system may not be limited to arrangements such as Medicare (private or public) or other similar mechanisms used in the private industry, but rather may be used to detect fraudulent activities in any healthcare arrangement.

For example, the healthcare fraud management system may process the claim using sets of rules, selected based on information relating to a claim type and the other information, to generate fraud information. The healthcare fraud management system may output the fraud information to the claims processor to inform the claims processor whether the particular claim potentially involves fraud. The fraud information may take the form of a fraud score or may take the form of an "accept" alert (meaning that the particular claim is not fraudulent) or a "reject" alert (meaning that the particular claim is potentially fraudulent or that "improper payments" were paid for the particular claim). The claims processor may then decide whether to pay the particular claim or challenge/deny payment for the particular claim based on the fraud information.

In some scenarios, the healthcare fraud management system may detect potential fraud in near real-time (i.e., while the claim is being submitted and/or processed). In other scenarios, the healthcare fraud management system may detect potential fraud after the claim is submitted (perhaps minutes, hours, or days later) but prior to payment of the claim. In either scenario, the healthcare fraud management system may reduce financial loss contributable to healthcare fraud. In addition, the healthcare fraud management system may help reduce health insurer costs in terms of software, hardware, and personnel dedicated to healthcare fraud detection and prevention.

Figure 2:
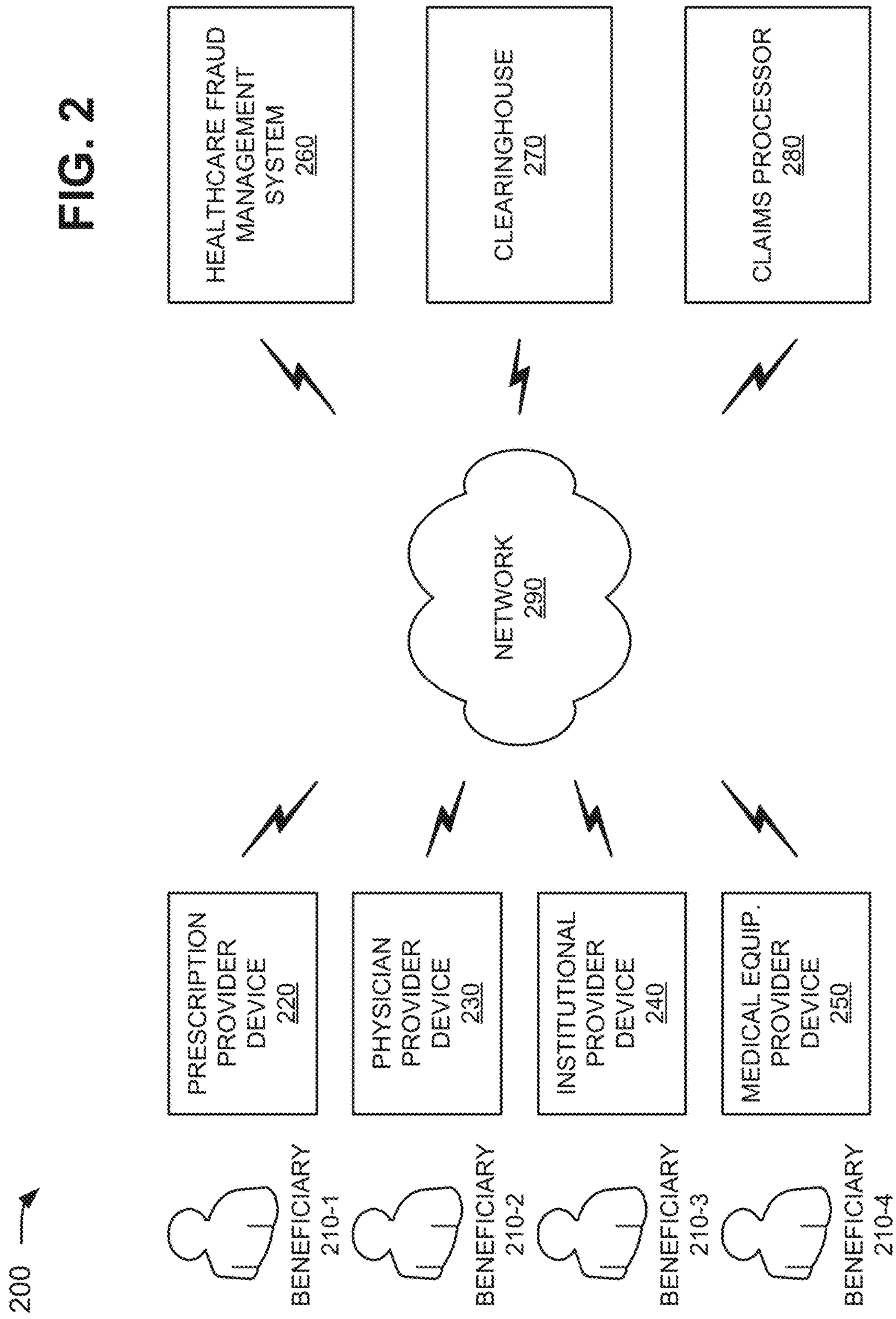
FIG. 2 is a diagram that illustrates an example environment in which systems and/or methods, described herein, may be implemented.

FIG. 2 is a diagram that illustrates an example environment 200 in which systems and/or methods, described herein, may be implemented. As shown in FIG. 2, environment 200 may include beneficiaries 210-1, . . . , 210-4 (collectively referred to as "beneficiaries 210," and individually as "beneficiary 210"), a prescription provider device 220, a physician provider device 230, an institutional provider device 240, a medical equipment provider device 250, a healthcare fraud management system 260, a clearinghouse 270, a claims processor 280, and a network 290.

While FIG. 2 shows a particular number and arrangement of devices, in practice, environment 200 may include additional devices, fewer devices, different devices, or differently arranged devices than are shown in FIG. 2. Also, although certain connections are shown in FIG. 2, these connections are simply examples and additional or different connections may exist in practice. Each of the connections may be a wired and/or wireless connection. Further, each prescription provider device 220, physician provider device 230, institutional provider device 240, and medical equipment provider device 250 may be implemented as multiple, possibly distributed, devices.

Beneficiary 210 may include a person, a business, an organization, or some other type of entity that receives healthcare services, such as services provided by a prescription provider, a physician provider, an institutional provider, a medical equipment provider, etc. For example, beneficiary 210 may receive prescription drugs, surgical procedures, doctor's office visits, physicals, hospital care, medical equipment, etc. from one or more providers.

Prescription provider device 220 may include a device, or a collection of devices, capable of interacting with clearinghouse 270 to submit a healthcare claim associated with healthcare services provided to a beneficiary 210 by a prescription provider. For example, prescription provider device 220 may correspond to a communication device (e.g., a mobile phone, a smartphone, a personal digital assistant (PDA), or a wireline telephone), a computer device (e.g., a laptop computer, a tablet computer, or a personal computer), a gaming device, a set top box, or another type of communication or computation device. As described herein, a prescription provider may use prescription provider device 220 to submit a healthcare claim to clearinghouse 270.

Physician provider device 230 may include a device, or a collection of devices, capable of interacting with clearinghouse 270 to submit a healthcare claim associated with healthcare services provided to a beneficiary 210 by a physician provider. For example, physician provider device 230 may correspond to a computer device (e.g., a server, a laptop computer, a tablet computer, or a personal computer). Additionally, or alternatively, physician provider device 230 may include a communication device (e.g., a mobile phone, a smartphone, a PDA, or a wireline telephone) or another type of communication or computation device. As described herein, a physician provider may use physician provider device 230 to submit a healthcare claim to clearinghouse 270.

Institutional provider device 240 may include a device, or a collection of devices, capable of interacting with clearinghouse 270 to submit a healthcare claim associated with healthcare services provided to a beneficiary 210 by an institutional provider. For example, institutional provider device 240 may correspond to a computer device (e.g., a server, a laptop computer, a tablet computer, or a personal computer). Additionally, or alternatively, institutional provider device 240 may include a communication device (e.g., a mobile phone, a smartphone, a PDA, or a wireline telephone) or another type of communication or computation device. As described herein, an institutional provider may use institutional provider device 240 to submit a healthcare claim to clearinghouse 270.

Healthcare fraud management system 260 may include a device, or a collection of devices, that performs fraud analysis on healthcare claims in near real-time. Healthcare fraud management system 260 may receive claims information from clearinghouse 270, may receive other healthcare information from other sources, may perform fraud analysis with regard to the claims information and in light of the other information and claim types, and may provide, to claims processor 280, information regarding the results of the fraud analysis.

In one implementation, healthcare fraud management system 260 may provide near real-time fraud detection tools with predictive modeling and risk scoring, and may provide end-to-end case management and claims review processes. Healthcare fraud management system 260 may also provide comprehensive reporting and analytics. Healthcare fraud management system 260 may monitor healthcare claims, prior to payment, in order to detect fraudulent activities before claims are forwarded to adjudication systems, such as claims processor 280.

Clearinghouse 270 may include a device, or a collection of devices, that receives healthcare claims from a provider, such as one of provider devices 220-250, makes minor edits to the claims, and provides the edited claims to healthcare fraud management system 260 or to claims processor 280 and then to healthcare fraud management system 260. In one example, clearinghouse 270 may receive a healthcare claim from one of provider devices 220-250, and may check the claim for minor errors, such as incorrect beneficiary information, incorrect insurance information, etc. Once the claim is checked and no minor errors are discovered, clearinghouse 270 may securely transmit the claim to healthcare fraud management system 260.

Claims processor 280 may include a device, or a collection of devices, that receives a claim, and information regarding the results of the fraud analysis for the claim, from healthcare fraud management system 260. If the fraud analysis indicates that the claim is not fraudulent, claims processor 280 may process, edit, and/or pay the claim. However, if the fraud analysis indicates that the claim may be fraudulent, claims processor 280 may deny the claim and may perform a detailed review of the claim. The detailed analysis of the claim by claims processor 280 may be further supported by reports and other supporting documentation provided by healthcare fraud management system 260.

Network 290 may include any type of network or a combination of networks. For example, network 290 may include a local area network (LAN), a wide area network (WAN) (e.g., the Internet), a metropolitan area network (MAN), an ad hoc network, a telephone network (e.g., a Public Switched Telephone Network (PSTN), a cellular network, or a voice-over-IP (VoIP) network), an optical network (e.g., a FiOS network), or a combination of networks. In one implementation, network 290 may support secure communications between provider devices 220-250, healthcare fraud management system 260, clearinghouse 270, and/or claims processor 280. These secure communications may include encrypted communications, communications via a private network (e.g., a virtual private network (VPN) or a private IP VPN (PIP VPN)), other forms of secure communications, or a combination of secure types of communications.

Figure 3:
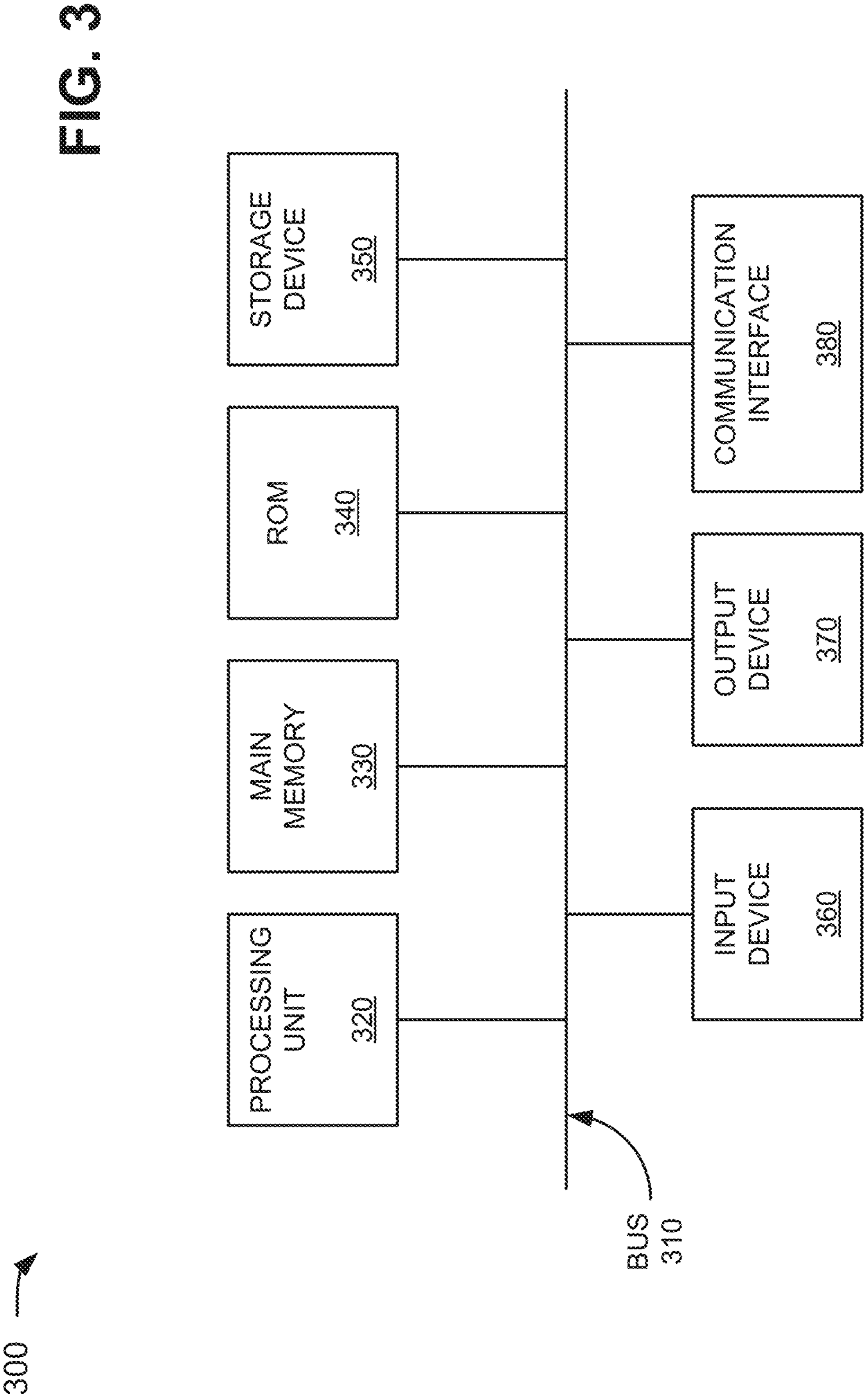
FIG. 3 is a diagram of example components of a device that may be used within the environment of FIG. 2.

FIG. 3 is a diagram of example components of a device 300. Device 300 may correspond to prescription provider device 220, physician provider device 230, institutional provider device 240, medical equipment provider device 250, healthcare fraud management system 260, clearinghouse 270, or claims processor 280. Each of prescription provider device 220, physician provider device 230, institutional provider device 240, medical equipment provider device 250, healthcare fraud management system 260, clearinghouse 270, and claims processor 280 may include one or more devices 300. As shown in FIG. 3, device 300 may include a bus 310, a processor 320, a main memory 330, a read only memory (ROM) 340, a storage device 350, an input device 360, an output device 370, and a communication interface 380.

Bus 310 may include a path that permits communication among the components of device 300. Processor 320 may include one or more processors, one or more microprocessors, one or more application specific integrated circuits (ASICs), one or more field programmable gate arrays (FPGAs), or one or more other types of processors that interpret and execute instructions. Main memory 330 may include a random access memory (RAM) or another type of dynamic storage device that stores information or instructions for execution by processor 320. ROM 340 may include a ROM device or another type of static storage device that stores static information or instructions for use by processor 320. Storage device 350 may include a magnetic storage medium, such as a hard disk drive, or a removable memory, such as a flash memory.

Input device 360 may include a mechanism that permits an operator to input information to device 300, such as a control button, a keyboard, a keypad, or another type of input device. Output device 370 may include a mechanism that outputs information to the operator, such as a light emitting diode (LED), a display, or another type of output device. Communication interface 380 may include any transceiver-like mechanism that enables device 300 to communicate with other devices or networks (e.g., network 290). In one implementation, communication interface 380 may include a wireless interface and/or a wired interface.

Device 300 may perform certain operations, as described in detail below. Device 300 may perform these operations in response to processor 320 executing software instructions contained in a computer-readable medium, such as main memory 330. A computer-readable medium may be defined as a non-transitory memory device. A memory device may include space within a single physical memory device or spread across multiple physical memory devices.

The software instructions may be read into main memory 330 from another computer-readable medium, such as storage device 350, or from another device via communication interface 380. The software instructions contained in main memory 330 may cause processor 320 to perform processes that will be described later. Alternatively, hardwired circuitry may be used in place of or in combination with software instructions to implement processes described herein. Thus, implementations described herein are not limited to any specific combination of hardware circuitry and software.

Although FIG. 3 shows example components of device 300, in other implementations, device 300 may include fewer components, different components, differently arranged components, and/or additional components than those depicted in FIG. 3. Alternatively, or additionally, one or more components of device 300 may perform one or more tasks described as being performed by one or more other components of device 300.

Figure 4:
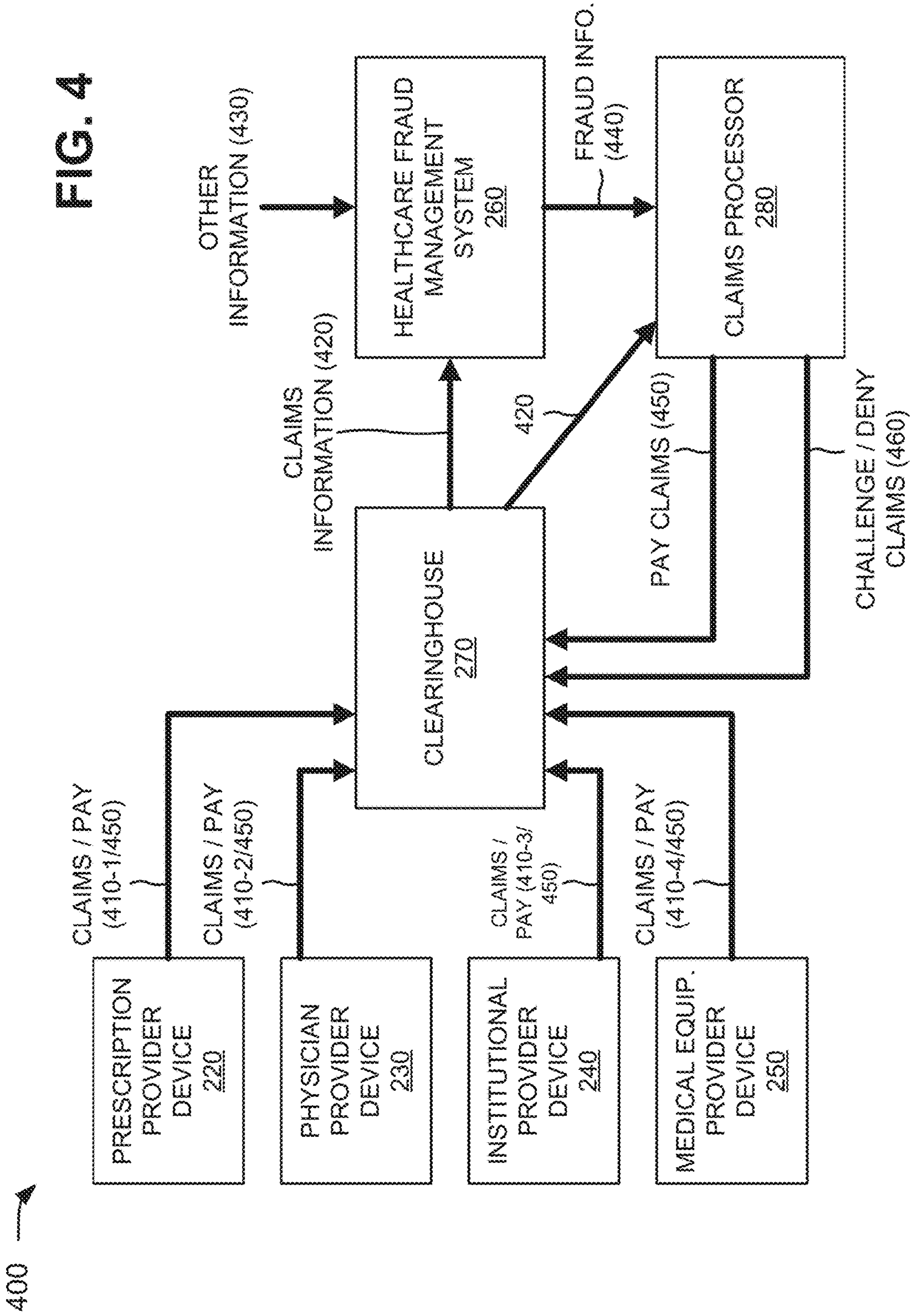
FIG. 4 is a diagram of example interactions between components of an example portion of the environment depicted in FIG. 2.

FIG. 4 is a diagram of example interactions between components of an example portion 400 of environment 200. As shown, example portion 400 may include prescription provider device 220, physician provider device 230, institutional provider device 240, medical equipment provider device 250, healthcare fraud management system 260, clearinghouse 270, and claims processor 280. Prescription provider device 220, physician provider device 230, institutional provider device 240, medical equipment provider device 250, healthcare fraud management system 260, clearinghouse 270, and claims processor 280 may include the features described above in connection with, for example, one or more of FIGS. 2 and 3.

Beneficiaries (not shown) may or may not receive healthcare services from a provider associated with prescription provider device 220, physician provider device 230, institutional provider device 240, and/or medical equipment provider device 250. As further shown in FIG. 4, whether or not the providers legitimately provided the healthcare services to the beneficiaries, prescription provider device 220 may generate claims 410-1, physician provider device 230 may generate claims 410-2, institutional provider device 240 may generate claims 410-3, and medical equipment provider device 250 may generate claims 410-4. Claims 410-1, . . . , 410-4 (collectively referred to herein as "claims 410," and, in some instances, singularly as "claim 410") may be provided to clearinghouse 270. Claims 410 may include interactions of a provider with clearinghouse 270, claims processor 280, or another entity responsible for paying for a beneficiary's healthcare or medical expenses, or a portion thereof. Claims 410 may be either legitimate or fraudulent.

Clearinghouse 270 may receive claims 410, may make minor changes to claims 410, and may provide claims information 420 to healthcare fraud management system 260 or to claims processor 280 and then to healthcare fraud management system 260. Claims information 420 may include provider information, beneficiary information, healthcare service information, etc. In one implementation, each claim 410 may involve a one-time exchange of information, between clearinghouse 270 and healthcare fraud management system 260, which may occur in near real-time to submission of claim 410 to clearinghouse 270 and prior to payment of claim 410. Alternatively, or additionally, each claim 410 may involve a series of exchanges of information, between clearinghouse 270 and healthcare fraud management system 260, which may occur prior to payment of claim 410.

Healthcare fraud management system 260 may receive claims information 420 from clearinghouse 270 and may obtain other information 430 regarding healthcare fraud from other systems. For example, other information 430 may include information associated with providers under investigation for possible fraudulent activities, information associated with providers who previously committed fraud, information provided by ZPICs, information provided by recovery audit contractors, and information provided by other external data sources. The information provided by the other external data sources may include an excluded provider list (EPL), a federal investigation database (FID), compromised provider and beneficiary identification (ID) numbers, compromised number contractor (CNC) information, benefit integrity unit (BIU) information, provider enrollment (PECOS) system information, and information from common working file (CWF) and claims adjudication systems. Healthcare fraud management system 260 may use claims information 420 and other information 430 to facilitate the processing of a particular claim 410.

For example, healthcare fraud management system 260 may process the particular claim 410 using sets of rules, selected based on information relating to a determined claim type and based on other information 430, to generate fraud information 440. Depending on the determined claim type associated with the particular claim 410, healthcare fraud management system 260 may select one or more of a procedure frequency rule, a geographical dispersion of services rule, a geographical dispersion of participants rule, a beneficiary frequency on provider rule, an auto summation of provider procedure time rule, a suspect beneficiary ID theft rule, an aberrant practice patterns rule, etc. Examples of such rules are described below in connection with FIG. 7. In one implementation, healthcare fraud management system 260 may process the particular claim 410 against a set of rules sequentially or in parallel. Healthcare fraud management system 260 may output fraud information 440 to claims processor 280 to inform claims processor 280 whether the particular claim 410 is potentially fraudulent. Fraud information 440 may include a fraud score, a fraud report, an "accept" alert (meaning that the particular claim 410 is not fraudulent), or a "reject" alert (meaning that the particular claim 410 is potentially fraudulent or improper payments were made for the particular claim). Claims processor 280 may then decide whether to pay the particular claim 410, as indicated by reference number 450, or challenge/deny payment for the particular claim 410, as indicated by reference number 460, based on fraud information 440.

In one implementation, healthcare fraud management system 260 may output fraud information 440 to clearinghouse 270 to inform clearinghouse 270 whether the particular claim 410 is potentially fraudulent. If fraud information 440 indicates that the particular claim 410 is fraudulent, clearinghouse 270 may reject the particular claim 410 and may provide an indication of the rejection to one of provider devices 220-250.

Alternatively, or additionally, healthcare fraud management system 260 may output (e.g., after payment of the particular claim 410) fraud information 440 to a claims recovery entity (e.g., a ZPIC or a recovery audit contractor) to inform the claims recovery entity whether the particular claim 410 is potentially fraudulent. If fraud information 440 indicates that the particular claim 410 is fraudulent, the claims recovery entity may initiate a claims recovery process to recover the money paid for the particular claim 410.

Although FIG. 4 shows example components of example portion 400, in other implementations, example portion 400 may include fewer components, different components, differently arranged components, and/or additional components than those depicted in FIG. 4. Alternatively, or additionally, one or more components of example portion 400 may perform one or more tasks described as being performed by one or more other components of example portion 400.

Figure 5:
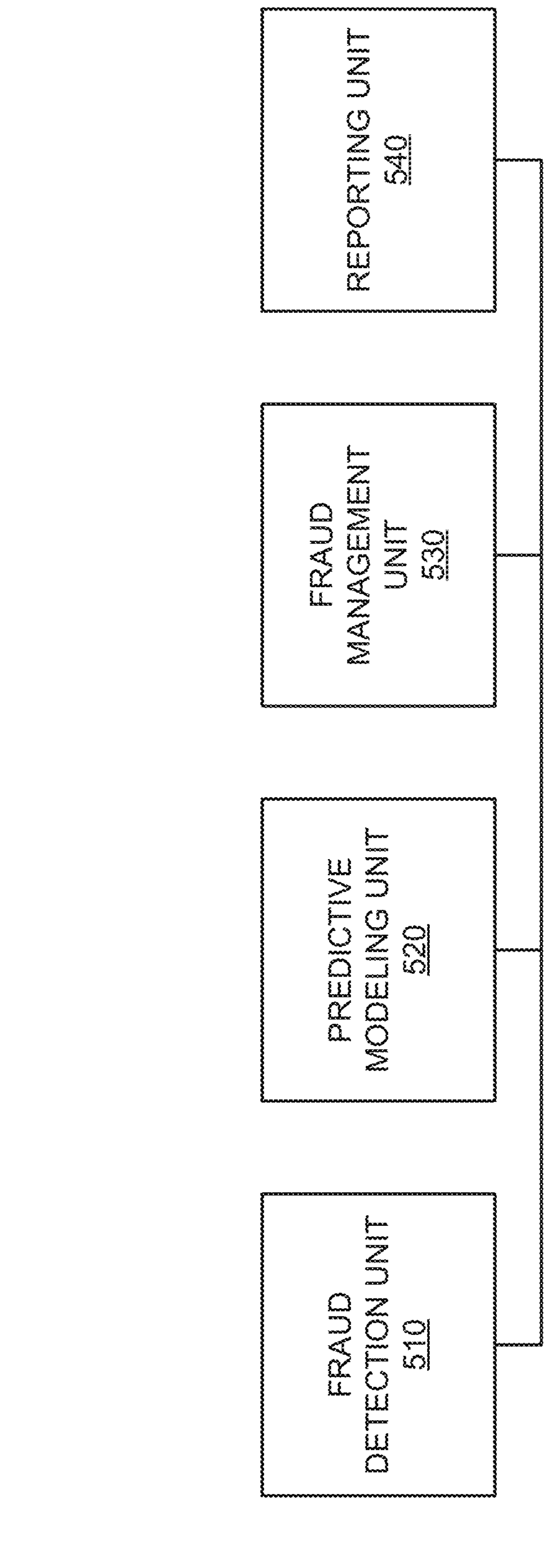
FIG. 5 is a diagram of example functional components of a healthcare fraud management system of FIG. 2.

FIG. 5 is a diagram of example functional components of healthcare fraud management system 260. In one implementation, the functions described in connection with FIG. 5 may be performed by one or more components of device 300 (FIG. 3) or by one or more devices 300. As shown in FIG. 5, healthcare fraud management system 260 may include a fraud detection unit 510, a predictive modeling unit 520, a fraud management unit 530, and a reporting unit 540. Fraud detection unit 510, predictive modeling unit 520, fraud management unit 530, and reporting unit 540 will be described generally with regard to FIG. 5 and will be described in more detail with regard to FIGS. 6-11.

Generally, fraud detection unit 510 may receive claims information 420 from clearinghouse 270, may receive other information 430 from other sources, and may analyze claims 410, in light of other information 430 and claim types, to determine whether claims 410 are potentially fraudulent. In one implementation, fraud detection unit 510 may generate a fraud score for a claim 410, and may classify a claim 410 as "safe," "unsafe," or "for review," based on the fraud score. A "safe" claim may include a claim 410 with a fraud score that is less than a first threshold (e.g., less than 5, less than 10, less than 20, etc. within a range of fraud scores of 0 to 100, where a fraud score of 0 may represent a 0% probability that claim 410 is fraudulent and a fraud score of 100 may represent a 100% probability that the claim is fraudulent). An "unsafe" claim may include a claim 410 with a fraud score that is greater than a second threshold (e.g., greater than 90, greater than 80, greater than 95, etc. within the range of fraud scores of 0 to 100) (where the second threshold is greater than the first threshold). A "for review" claim may include a claim 410 with a fraud score that is greater than a third threshold (e.g., greater than 50, greater than 40, greater than 60, etc. within the range of fraud scores of 0 to 100) and not greater than the second threshold (where the third threshold is greater than the first threshold and less than the second threshold). In one implementation, the first, second, and third thresholds and the range of potential fraud scores may be set by an operator of healthcare fraud management system 260. Alternatively, or additionally, the first, second, and/or third thresholds and/or the range of potential fraud scores may be set by clearinghouse 270 and/or claims processor 280. In this case, the thresholds and/or range may vary from clearinghouse-to-clearinghouse and/or from claims processor-to-claims processor. The fraud score may represent a probability that a claim is fraudulent.

If fraud detection unit 510 determines that a claim 410 is a "safe" claim, fraud detection unit 510 may notify claims processor 280 that claims processor 280 may safely approve, or alternatively fulfill, claim 410. If fraud detection unit 510 determines that a claim 410 is an "unsafe" claim, fraud detection unit 510 may notify claims processor 280 to take measures to minimize the risk of fraud (e.g., deny claim 410, request additional information from one or more provider devices 220-250, require interaction with a human operator, refuse to fulfill a portion of claim 410, etc.). Alternatively, or additionally, fraud detection unit 510 may provide information regarding the unsafe claim to predictive modeling unit 520 and/or fraud management unit 530 for additional processing of claim 410. If fraud detection unit 510 determines that a claim 410 is a "for review" claim, fraud detection unit 410 may provide information regarding claim 410 to predictive modeling unit 520 and/or fraud management unit 530 for additional processing of claim 410.

In one implementation, fraud detection unit 510 may operate within the claims processing flow between clearinghouse 270 and claims processor 280, without creating processing delays. Fraud detection unit 510 may analyze and investigate claims 410 in real time or near real-time, and may refer "unsafe" claims or "for review" claims to a fraud case management team for review by clinical staff. Claims 410 deemed to be fraudulent may be delivered to claims processor 280 (or other review systems) so that payment can be suspended, pending final verification or appeal determination.

Generally, predictive modeling unit 520 may receive information regarding certain claims 410 and may analyze these claims 410 to determine whether the certain claims 410 are fraudulent. In one implementation, predictive modeling unit 520 may provide a high volume, streaming data reduction platform for claims 410. Predictive modeling unit 520 may receive claims 410, in real time or near real-time, and may apply claim type-specific predictive models, configurable edit rules, artificial intelligence techniques, and/or fraud scores to claims 410 in order to identify inappropriate patterns and outliers.

With regard to data reduction, predictive modeling unit 520 may normalize and filter claims information 420 and/or other information 430 (e.g., to a manageable size), may analyze the normalized/filtered information, may prioritize the normalized/filtered information, and may present a set of suspect claims 410 for investigation. The predictive models applied by predictive modeling unit 520 may support linear pattern recognition techniques (e.g., heuristics, expert rules, etc.) and non-linear pattern recognition techniques (e.g., neural nets, clustering, artificial intelligence, etc.). Predictive modeling unit 520 may assign fraud scores to claims 410, may create and correlate alarms across multiple fraud detection methods, and may prioritize claims 410 (e.g., based on fraud scores) so that claims 410 with the highest risk of fraud may be addressed first.

Generally, fraud management unit 530 may provide a holistic, compliant, and procedure-driven operational architecture that enables extraction of potentially fraudulent healthcare claims for more detailed review. Fraud management unit 530 may refer potentially fraudulent claims to trained analysts who may collect information (e.g., from healthcare fraud management system 260) necessary to substantiate further disposition of the claims. Fraud management unit 530 may generate key performance indicators (KPIs) that measure performance metrics for healthcare fraud management system 260 and/or the analysts.

In one implementation, fraud management unit 530 may provide lists of prioritized healthcare claims under review with supporting aggregated data, and may provide alerts and associated events for a selected healthcare claim. Fraud management unit 530 may provide notes and/or special handling instructions for a provider and/or beneficiary associated with a claim under investigation. Fraud management unit 530 may also provide table management tools (e.g., thresholds, exclusions, references, etc.), account management tools (e.g., roles, filters, groups, etc.), and geographical mapping tools and screens (e.g., for visual analysis) for healthcare claims under review.

Generally, reporting unit 540 may generate comprehensive standardized and ad-hoc reports for healthcare claims analyzed by healthcare fraud management system 260. For example, reporting unit 540 may generate financial management reports, trend analytics reports, return on investment reports, KPI/performance metrics reports, intervention analysis/effectiveness report, etc. Reporting unit 540 may provide data mining tools and a data warehouse for performing trending and analytics for healthcare claims. Information provided in the data warehouse may include alerts and case management data associated with healthcare claims. Such information may be available to claims analysts for trending, post data analysis, and additional claims development, such as preparing a claim for submission to program safeguard contractors (PSCs) and other authorized entities. In one example, information generated by reporting unit 540 may be used by fraud detection unit 510 and predictive modeling unit 520 to update rules, predictive models, artificial intelligence techniques, and/or fraud scores generated by fraud detection unit 510 and/or predictive modeling unit 520.

Although FIG. 5 shows example functional components of healthcare fraud management system 260, in other implementations, healthcare fraud management system 260 may include fewer functional components, different functional components, differently arranged functional components, and/or additional functional components than those depicted in FIG. 5. Alternatively, or additionally, one or more functional components of healthcare fraud management system 260 may perform one or more tasks described as being performed by one or more other functional components of healthcare fraud management system 260.

Figure 6:
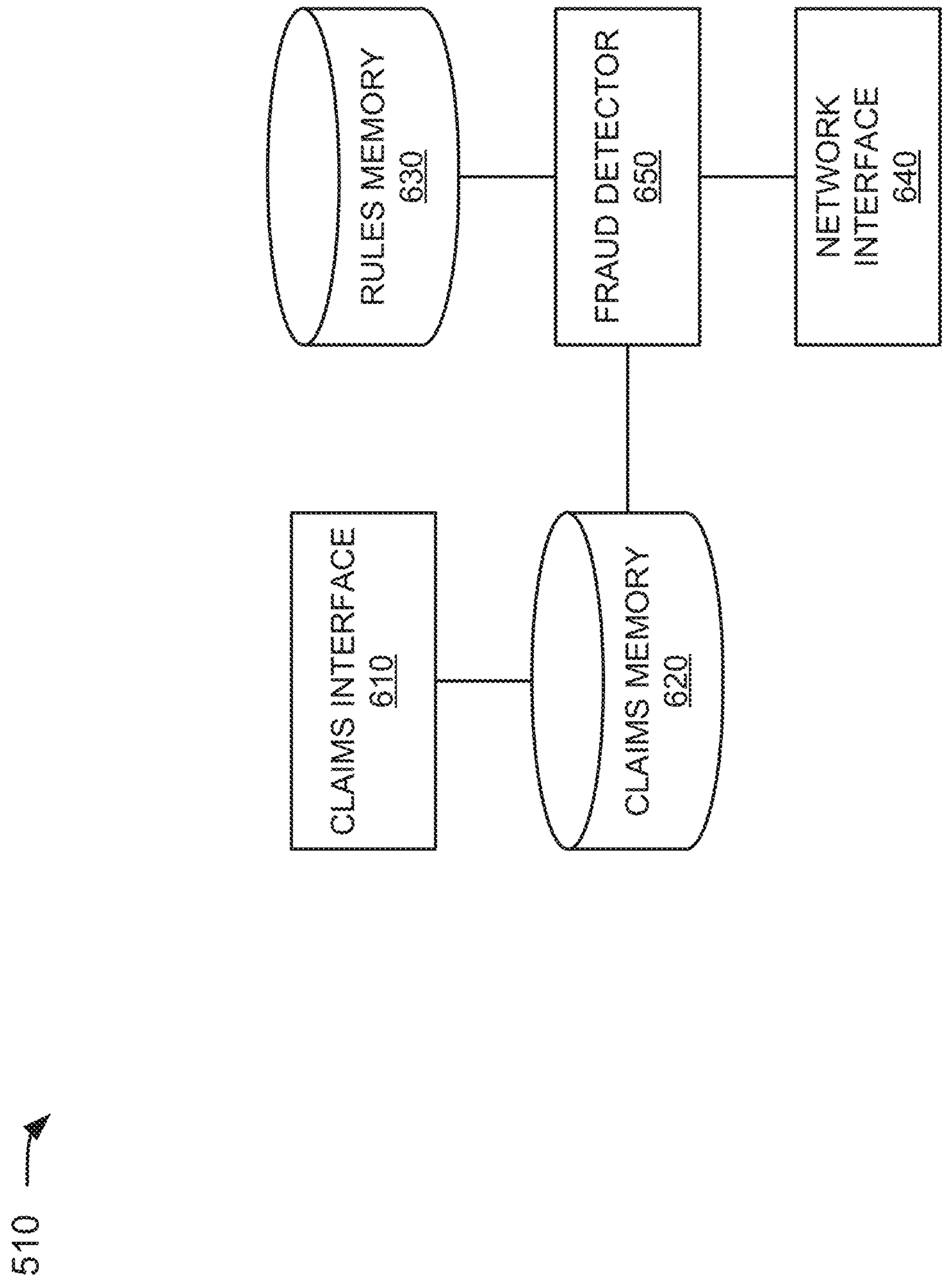
FIG. 6 is a diagram of example functional components of a fraud detection unit of FIG. 5.

FIG. 6 is a diagram of example functional components of fraud detection unit 510. In one implementation, the functions described in connection with FIG. 6 may be performed by one or more components of device 300 (FIG. 3) or by one or more devices 300. As shown in FIG. 6, fraud detection unit 510 may include a claims interface component 610, a claims memory 620, a rules memory 630, a network interface component 640, and a fraud detector component 650.

Claims interface component 610 may include a device, or a collection of devices, that may interact with clearinghouse 270 and claims processor 280 to assist the users of clearinghouse 270 and claims processor 280 in using healthcare fraud management system 260. For example, claims interface component 610 may exchange encryption information, such as public/private keys or VPN information, with clearinghouse 270 and/or claims processor 280 to permit secure future communications between healthcare fraud management system 260 and clearinghouse 270 and/or claims processor 280.

Claims interface component 610 may receive, from clearinghouse 270 or other systems, information that might be useful in detecting a fraudulent healthcare claim. For example, claims interface component 610 may receive claims information 420 from clearinghouse 270 and may obtain other information 430 regarding healthcare fraud from other systems. Other information 430 may include a black list (e.g., a list of beneficiaries or providers that are known to be associated with fraudulent activity) and/or a white list (e.g., a list of beneficiaries or providers that are known to be particularly trustworthy). Additionally, or alternatively, other information 430 may include historical records of claims associated with beneficiaries or providers. These historical records may include information regarding claims that were processed by a system other than healthcare fraud management system 260. Additionally, or alternatively, claims interface component 610 may receive a set of policies from clearinghouse 270 and/or claims processor 280. The policies may indicate thresholds for determining safe claims, unsafe claims, and for review claims, may indicate a range of possible fraud scores (e.g., range of 0 to 100, range of 0 to 1000, etc.), or may indicate other business practices of beneficiaries and/or providers. Additionally, or alternatively, claims interface component 610 may receive a set of rules that are particular to a beneficiary or a provider.

Claims memory 620 may include one or more memory devices to store information regarding present and/or past claims. Present claims may include claims currently being processed by fraud detector component 650, and past claims may include claims previously processed by fraud detector component 650. In one implementation, claims memory 620 may store data in the form of a database, such as a relational database or an object-oriented database. Alternatively, or additionally, claims memory 620 may store data in a non-database manner, such as tables, linked lists, or another arrangement of data.

Claims memory 620 may store a variety of information for any particular claim. For example, claims memory 620 might store: information identifying a provider or one of provider devices 220-250 (e.g., a provider device ID, an IP address associated with the provider device, a telephone number associated with the provider device, a username associated with the provider, a provider ID, etc.); information identifying a beneficiary (e.g., a beneficiary ID, a beneficiary name, a beneficiary address, etc.); information identifying a type of provider (e.g., a prescription provider, a physician provider, an institutional provider, a medical equipment provider, etc.); a name, telephone number, and address associated with the provider; a dollar amount of the claim; line items of the claim (e.g., identification of each good/service purchased, healthcare procedure codes associated with the claim, etc.); information regarding insurance provided by a beneficiary (e.g., an insurance company name, an insurance company address, a group number, a medical record number, etc.); a day and/or time that the good/service associated with the claim was provided (e.g., 13:15 on 03/05/2011); a geographic location associated with the beneficiary or the provider, and/or other types of information associated with the claim, the provider, one of provider devices 220-250, or the beneficiary, and/or past claims associated with the claim, the provider, one of provider devices 220-250, or the beneficiary.

Claims memory 620 may also store other information that might be useful in detecting a fraudulent healthcare claim. For example, claims memory 620 may store black lists and/or white lists. The black/white lists may be particular to a provider or a beneficiary or may be applicable across providers or beneficiaries. The black/white lists may be received from other systems or may be generated by healthcare fraud management system 260.

Claims memory 620 may also store historical records of claims from providers. These historical records may include claims that were processed by a system other than healthcare fraud management system 260. The historical records may include information similar to the information identified above and may also include information regarding claims that had been identified as fraudulent.

Rules memory 630 may include one or more memory devices to store information regarding rules that may be applicable to claims. In one implementation, rules memory 630 may store rules in one or more libraries. A "library" may be a block of memory locations (contiguous or non-contiguous memory locations) that stores a set of related rules. Alternatively, or additionally, rules memory 630 may store rules in another manner (e.g., as database records, tables, linked lists, etc.).

The rules may include general rules, provider-specific rules, beneficiary-specific rules, claim attribute specific rules, single claim rules, multi-claim rules, heuristic rules, pattern recognition rules, and/or other types of rules. Some rules may be applicable to all claims (e.g., general rules may be applicable to all claims), while other rules may be applicable to a specific set of claims (e.g., provider-specific rules may be applicable to claims associated with a particular provider). Rules may be used to process a single claim (meaning that the claim may be analyzed for fraud without considering information from another claim) or may be used to process multiple claims (meaning that the claim may be analyzed for fraud by considering information from another claim). Rules may also be applicable for multiple, unaffiliated providers (e.g., providers having no business relationships) or multiple, unrelated beneficiaries (e.g., beneficiaries having no familial or other relationship).

Figure 7:
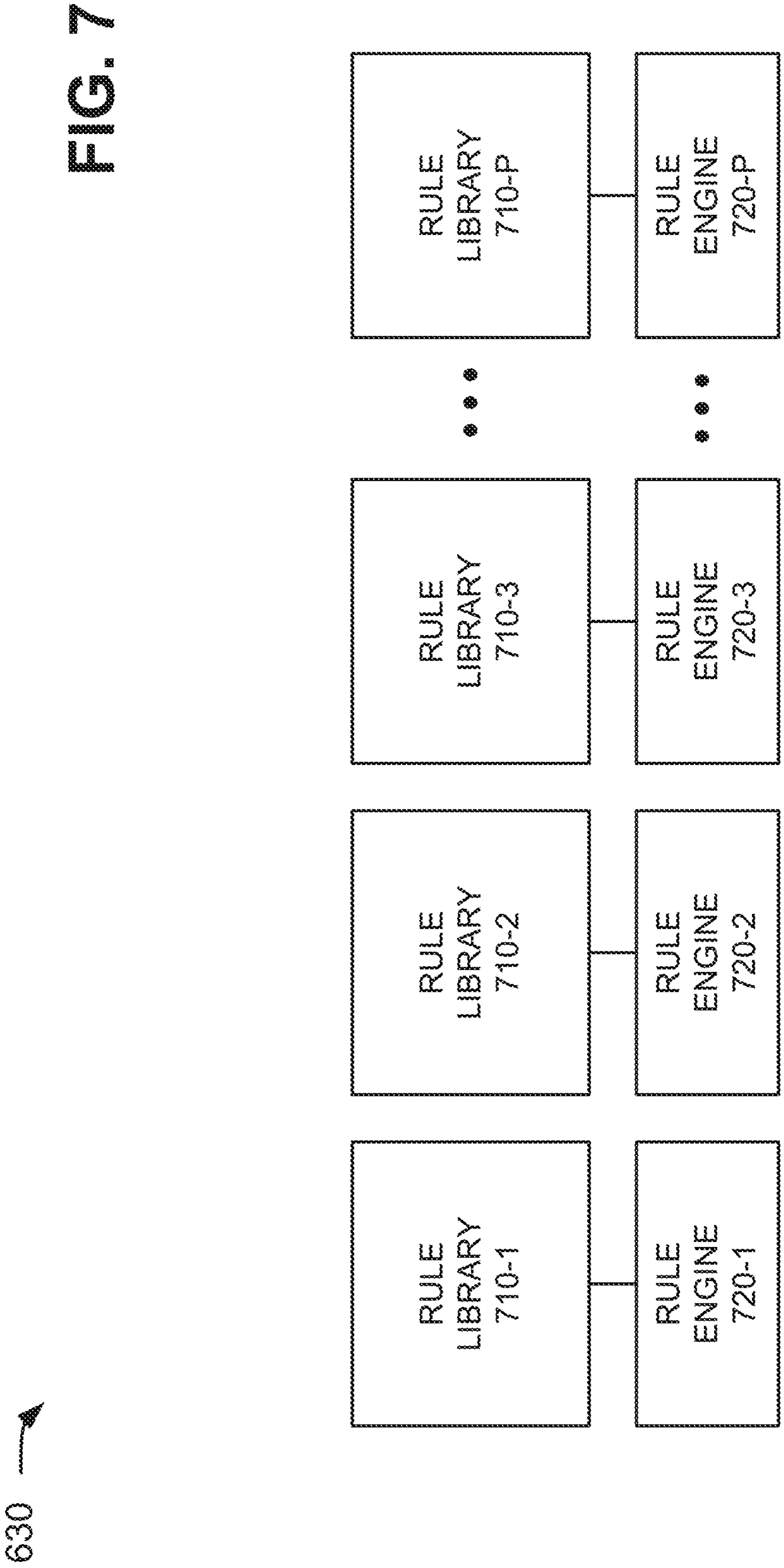
FIG. 7 is a diagram of example libraries that may be present within a rules memory of FIG. 6.

FIG. 7 is a diagram of example libraries that may be present within rules memory 630. As shown in FIG. 7, rules memory 630 may include rule libraries 710-1, 710-2, 710-3, . . . 710-P (P≥1) (collectively referred to as "libraries 710," and individually as "library 710") and rule engines 720-1, 720-2, 720-3, . . . 720-P (collectively referred to as "rule engines 720," and individually as "rule engine 720"). While FIG. 7 illustrates that rules memory 630 includes a set of rule libraries 710 and a corresponding set of rule engines 720, rules memory 630 may include fewer components, additional components, or different components in another implementation.

Each rule library 710 may store a set of related rules. For example, a rule library 710 may store general rules that are applicable to all claims. Additionally, or alternatively, a rule library 710 may store rules applicable to a single claim (meaning that the claim may be analyzed for fraud without considering information from another claim). Additionally, or alternatively, a rule library 710 may store rules applicable to multiple claims (meaning that the claim may be analyzed for fraud by considering information from another claim (whether from the same provider or a different provider, whether associated with the same beneficiary or a different beneficiary)).

Additionally, or alternatively, a rule library 710 may store provider-specific rules. Provider-specific rules may include rules that are applicable to claims of a particular provider, and not applicable to claims of other providers. Additionally, or alternatively, a rule library 710 may store provider type-specific rules. Provider type-specific rules may include rules that are applicable to claims associated with a particular type of provider (e.g., a prescription provider, a physician provider, an institutional provider, a medical equipment provider, etc.), and not applicable to claims associated with other types of providers. Additionally, or alternatively, a rule library 710 may store beneficiary-specific rules. Beneficiary-specific rules may include rules that are applicable to claims of a particular beneficiary or a particular set of beneficiaries (e.g., all beneficiaries in the beneficiary's family, all beneficiaries located at a particular geographic location, all beneficiaries located within a particular geographic region, etc.), and not applicable to claims of other beneficiaries or sets of beneficiaries.

Additionally, or alternatively, a rule library 710 may store procedure frequency-specific rules. Procedure frequency-specific rules may include rules that provide alerts for claims based on an excessive number (e.g., greater than a configurable threshold) of procedures or services performed for a single beneficiary in a configurable time period (e.g., a day, a week, a month, etc.). A priority associated with a claim may increase (e.g., indicating a more potentially fraudulent claim) as the number of procedures or services increases over the configurable threshold. Additionally, or alternatively, a rule library 710 may store geographical dispersion of services-specific rules. Geographical dispersion of services-specific rules may include rules that identify geographical anomalies between a beneficiary and providers based on time, distance, and frequency associated with a claim. Geographical dispersion of services-specific rules may provide alerts for a claim when a beneficiary receives a number of services (e.g., greater than a configurable threshold) from providers that are an improbable distance (e.g., greater than another threshold) from the beneficiary. A priority associated with a claim may increase (e.g., indicating a more potentially fraudulent claim) as a geographical dispersion between a beneficiary and a provider increases.

Additionally, or alternatively, a rule library 710 may store beneficiary frequency-specific rules. Beneficiary frequency-specific rules may include rules that provide alerts for claims when a single provider treats an excessive number (e.g., greater than a configurable threshold) of beneficiaries in a configurable time period (e.g., a day, a week, a month, etc.). A priority associated with a claim may increase (e.g., indicating a more potentially fraudulent claim) as the number of beneficiaries increases over the configurable threshold, as a variance from normal services provided by the provider increases, as a number of locations of the beneficiaries increases, etc.

Additionally, or alternatively, a rule library 710 may store single claim analysis-related rules. Single claim analysis-related rules may include rules that are applicable to suspected fraudulent providers and/or beneficiaries identified from sources, such as PECOs, EPL, vital statistics, etc. Additionally, or alternatively, a rule library 710 may store auto summation of provider procedure time-specific rules. Auto summation of provider procedure time-specific rules may include rules that identify a single provider who performs a number procedures that, when the procedure times are added together, exceed a probably work day for the provider. For example, the auto summation of provider procedure time-specific rules may identify a doctor who performs thirty (30) hours of surgery in a single day.

Additionally, or alternatively, a rule library 710 may store suspect beneficiary ID theft-specific rules. Suspect beneficiary ID theft-specific rules may include rules that identify a number of providers using the same beneficiary ID over a time period (e.g., a day, a week, etc.) but without specified place-of-service codes (e.g., hospital) and diagnosis codes. Suspect beneficiary ID theft-specific rules may include rules that identify a single beneficiary that receives an excessive number (e.g., greater than a configurable threshold by specialty) of procedures or services on the same day.

Additionally, or alternatively, a rule library 710 may store alert on suspect address-specific rules. Alert on suspect address-specific rules may include rules that correlate alerts based on national provider identifier (NPI) addresses to detect suspect addresses associated with providers and beneficiaries. Additionally, or alternatively, a rule library 710 may store inconsistent relationship-specific rules (e.g., a gynecological procedure performed on a male beneficiary), excessive cost-specific rules (e.g., costs for a beneficiary or a provider), etc.

Additionally, or alternatively, a rule library 710 may store rules that identify fraudulent therapies (e.g., physical therapy, occupational therapy, speech language pathology, psychotherapy, etc.) provided to groups of beneficiaries but which are claimed as if provided individually. Additionally, or alternatively, a rule library 710 may store rules that identify a "gang visit" fraud scheme. A gang visit may occur when providers (e.g., optometrists, podiatrists, etc.) visit most beneficiaries in a facility, without rendering any services, but bill as if services have been provided to all of the beneficiaries. Additionally, or alternatively, a rule library 710 may store rules that identify organized and coordinated healthcare fraud schemes, such as common surname origins for beneficiaries, a provider billing less than $10,000 per day, shared facilities among high risk providers, etc.

The rules in rule libraries 710 may include human-generated rules and/or automatically-generated rules. The automatically-generated rules may include heuristic rules and/or pattern recognition rules. Heuristic rules may include rules that have been generated by using statistical analysis, or the like, that involves analyzing a group of attributes (e.g., a pair of attributes or a tuple of attributes) of claims, and learning rules associated with combinations of attributes that are indicative of fraudulent claims. Pattern recognition rules may include rules that have been generated using machine learning, artificial intelligence, neural networks, decision trees, or the like, that analyzes patterns appearing in a set of training data, which includes information regarding claims that have been identified as fraudulent and information regarding claims that have been identified as non-fraudulent, and generates rules indicative of patterns associated with fraudulent claims.

Alternatively, or additionally, rule libraries 710 may store other types of rules, other combinations of rules, or differently-generated rules. Because fraud techniques are constantly changing, the rules, in rule libraries 710, may be regularly updated (either by manual or automated interaction) by modifying existing rules, adding new rules, and/or removing antiquated rules.

Each rule engine 720 may correspond to a corresponding rule library 710. A rule engine 720 may receive a claim from fraud detector component 650, coordinate the execution of the rules by the corresponding rule library 710, and return the results (in the form of zero or more alarms) to fraud detector component 650. In one implementation, rule engine 720 may cause a claim to be processed by a set of rules within the corresponding rule library 710 in parallel. In other words, the claim may be concurrently processed by multiple, different rules in a rule library 710 (rather than serially processed).

Returning to FIG. 6, network interface component 640 may include a device, or a collection of devices, that obtains, manages, and/or processes claims information 420 and other information 430, which may be used to facilitate the identification of fraudulent claims. Network interface component 640 may interact with clearinghouse 270 to obtain claims information 420, and may interact with other systems to obtain other information 430. In one implementation, network interface component 640 may store claims information 420 and other information 430 and perform look-ups within the stored information when requested by fraud detector component 650. Alternatively, or additionally, network interface component 640 may store claims information 420 and other information 430 and permit fraud detector component 650 to perform its own look-ups within the stored information. Network interface component 640 may store the information in the form of a database, such as a relational database or an object-oriented database. Alternatively, network interface component 640 may store the information in a non-database manner, such as tables, linked lists, or another arrangement of data.

Fraud detector component 650 may include a device, or a collection of devices, that performs automatic fraud detection on claims. Fraud detector component 650 may receive a claim (e.g., associated with one of provider devices 220-250) from clearinghouse 270, obtain other information 430 relevant to the claim, and select particular libraries 710 and particular rules within the selected libraries 710 applicable to the claim based on other information 430 and a claim type. Fraud detector component 650 may then provide the claim for processing by the selected rules in the selected libraries 710 in parallel. The output of the processing, by the selected libraries 710, may include zero or more alarms. An "alarm," as used herein, is intended to be broadly interpreted as a triggering of a rule in a library 710. A rule is triggered when the claim satisfies the rule. For example, assume that a rule indicates a situation where a doctor performs a number of hours of services in single day. Claims for such work would trigger (or satisfy) the rule if the claims involved more than twenty-four (24) hours of services in single day.

Fraud detector component 650 may sort and group the alarms and analyze the groups to generate a fraud score. The fraud score may reflect the probability that the claim is fraudulent. Fraud detector component 650 may send the fraud score, or an alert generated based on the fraud score, to claims processor 280 via fraud information 440. The alert may simply indicate that claims processor 280 should pay, deny, or further review the claim. In one implementation, the processing by fraud detector component 650 from the time that fraud detector component 650 receives the claim to the time that fraud detector component 650 sends the alert may be within a relatively short time period, such as, for example, within thirty seconds, sixty seconds, or ten seconds. Alternatively, or additionally, the processing by fraud detector component 650 from the time that fraud detector component 650 receives the claim to the time that fraud detector component 650 sends the alert may be within a relatively longer time period, such as, for example, within minutes, hours, or days.

Although FIG. 6 shows example functional components of fraud detection unit 510, in other implementations, fraud detection unit 510 may include fewer functional components, different functional components, differently arranged functional components, and/or additional functional components than those depicted in FIG. 6. Alternatively, or additionally, one or more functional components of fraud detection unit 510 may perform one or more tasks described as being performed by one or more other functional components of fraud detection unit 510.

Figure 8:
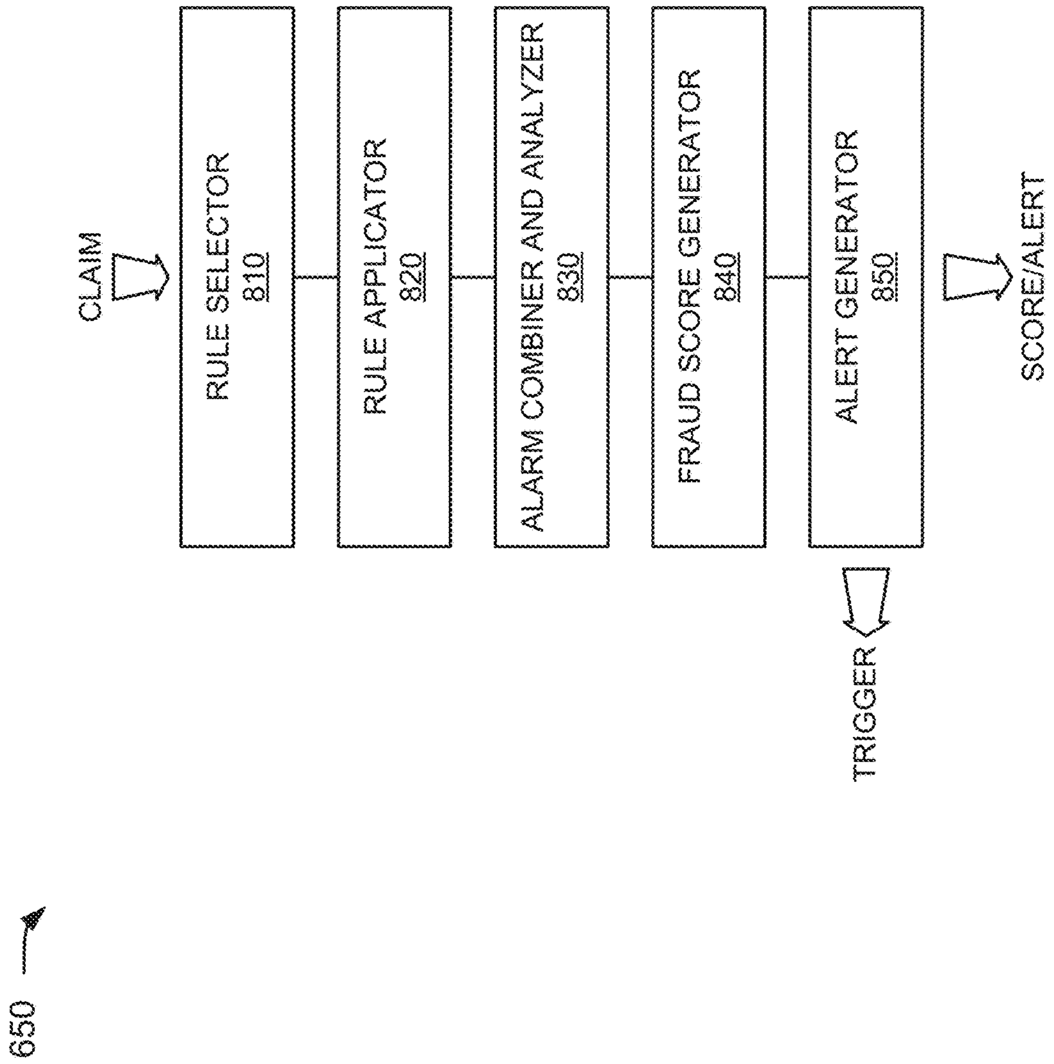
FIG. 8 is a diagram of example functional components of a fraud detector of FIG. 6.

FIG. 8 is a diagram of example functional components of fraud detector component 650. In one implementation, the functions described in connection with FIG. 8 may be performed by one or more components of device 300 (FIG. 3) or by one or more devices 300. As shown in FIG. 8, fraud detector component 650 may include a rule selector component 810, a rule applicator component 820, an alarm combiner and analyzer component 830, a fraud score generator component 840, and an alert generator component 850.

Rule selector component 810 may receive a claim 410 from clearinghouse 270 via claims information 420, and may determine a type (e.g., a prescription provider claim, a physician provider claim, an institutional provider claim, a medical equipment provider claim, etc.) associated with claim 410. In one implementation, claim 410 may include various information, such as information identifying a beneficiary (e.g., name, address, telephone number, etc.); a total dollar amount of claim 410; line items of claim 410 (e.g., information identifying a good or service purchased or rented, etc.); information identifying a provider (e.g., name, address, telephone number, etc.); and information identifying a day and/or time that claim 410 occurred or the services associated with claim 410 occurred (e.g., 13:15 on 04/05/2011).

Additionally, or alternatively, rule selector component 810 may receive other information (called "meta information") from clearinghouse 270 in connection with claim 410. For example, the meta information may include information identifying one of provider devices 220-250 (e.g., a provider device ID, an IP address associated with the provider device, a telephone number associated with the provider device, etc.); other information regarding one of provider devices 220-250 (e.g., a type/version of browser used by the provider device, cookie information associated with the provider device, a type/version of an operating system used by the provider device, etc.); and/or other types of information associated with claim 410, the provider, the provider device, or the beneficiary.

Additionally, or alternatively, rule selector component 810 may receive or obtain other information 430 regarding claim 410, the provider, the provider device, or the beneficiary. For example, other information 430 may include a geographic identifier (e.g., zip code or area code) that may correspond to the IP address associated with the provider device. Other information 430 may also, or alternatively, include information identifying a type of provider (e.g., a prescription provider, a physician provider, an institutional provider, a medical equipment provider, etc.). Rule selector component 810 may obtain other information 430 from a memory or may use research tools to obtain other information 430.

Additionally, or alternatively, rule selector component 810 may receive or obtain historical information regarding the provider, the provider device, the beneficiary, or information included in the claim. In one implementation, rule selector component 710 may obtain the historical information from claims memory 620 (FIG. 6).

The claim information, the meta information, the other information, and/or the historical information may be individually referred to as a "claim attribute" or an "attribute of the claim," and collectively referred to as "claim attributes" or "attributes of the claim."

Rule selector component 810 may generate a profile for claim 410 based on the claim attributes. Based on the claim profile and perhaps relevant information in a white or black list (i.e., information, relevant to the claim, that is present in a white or black list), rule selector component 810 may select a set of libraries 710 within rules memory 630 and/or may select a set of rules within one or more of the selected libraries 710. For example, rule selector component 810 may select libraries 710, corresponding to general rules, single claim rules, multi-claim rules, provider-specific rules, procedure frequency-specific rules, etc., for claim 410.

Rule applicator component 820 may cause claim 410 to be processed using rules of the selected libraries 710. For example, rule applicator component 820 may provide information regarding claim 410 to rule engines 720 corresponding to the selected libraries 710. Each rule engine 720 may process claim 410 in parallel and may process claim 410 using all or a subset of the rules in the corresponding library 710. Claim 410 may be concurrently processed by different sets of rules (of the selected libraries 710 and/or within each of the selected libraries 710). The output, of each of the selected libraries 710, may include zero or more alarms. As explained above, an alarm may be generated when a particular rule is triggered (or satisfied).

Alarm combiner and analyzer component 830 may aggregate and correlate the alarms. For example, alarm combiner and analyzer component 830 may analyze attributes of the claim(s) with which the alarms are associated (e.g., attributes relating to a number of procedures performed, geographical information of the provider and beneficiary, a number of beneficiaries, etc.). Alarm combiner and analyzer component 830 may sort the alarms, along with alarms of other claims (past or present), into groups (called "cases") based on values of one or more of the attributes of the claims associated with the alarms (e.g., provider names, geographic locations of providers and beneficiaries, beneficiary names, etc.). The claims, included in a case, may involve one provider or multiple, unaffiliated providers and/or one beneficiary or multiple, unrelated beneficiaries.

Alarm combiner and analyzer component 830 may separate alarms (for all claims, claims sharing a common claim attribute, or a set of claims within a particular window of time) into one or more cases based on claim attributes. For example, alarm combiner and analyzer component 830 may place alarms associated with a particular claim type into a first case, alarms associated with another particular claim type into a second case, alarms associated with a particular provider into a third case, alarms associated with a beneficiary into a fourth case, alarms associated with a particular type of medical procedure into a fifth case, alarms associated with a particular geographic location into a sixth case, etc. A particular alarm may be included in multiple cases.

For example, assume that fraud detector component 650 receives four claims CL1-CL4. By processing each of claims CL1-CL4 using rules in select libraries 710, zero or more alarms may be generated. It may be assumed that three alarms A1-A3 are generated. An alarm may be an aggregation of one or more claims (e.g., alarm A1 is the aggregation of claims CL1 and CL2; alarm A2 is the aggregation of claim CL3; and alarm A3 is the aggregation of claims CL3 and CL4) that share a common attribute. The alarms may be correlated into cases. It may further be assumed that two cases C1 and C2 are formed. A case is a correlation of one or more alarms (e.g., case C1 is the correlation of alarms A1 and A2; and case C2 is the correlation of alarms A2 and A3) that share a common attribute. An individual alarm may not be sufficient evidence to determine that a claim is fraudulent. When the alarm is correlated with other alarms in a case, then a clearer picture of whether the claim is fraudulent may be obtained. Further, when multiple cases involving different attributes of the same claim are analyzed, then a decision may be made whether a claim is potentially fraudulent.

Fraud score generator component 840 may generate a fraud score. Fraud score generator component 840 may generate a fraud score from information associated with one or more cases (each of which may include one or more claims and one or more alarms). In one implementation, fraud score generator component 840 may generate an alarm score for each generated alarm. For example, each of the claim attributes and/or each of the rules may have a respective associated weight value. Thus, when a particular claim attribute causes a rule to trigger, the generated alarm may have a particular score based on the weight value of the particular claim attribute and/or the weight value of the rule. When a rule involves multiple claims, the generated alarm may have a particular score that is based on a combination of the weight values of the particular claim attributes.

In one implementation, fraud score generator component 840 may generate a case score for a case by combining the alarm scores in some manner. For example, fraud score generator component 840 may generate a case score (CS) by using a log-based Naïve Bayesian algorithm, such as:

$$CS = \frac{\sum_i \frac{AS_i \times AW_i}{AM_i}}{\sum_i AW_i} \times 1000,$$

where CS may refer to the score for a case, $AS_i$ may refer to an alarm score for a given value within an alarm i, $AW_i$ may refer to a relative weight given to alarm i, and $AM_i$ may refer to a maximum score value for alarm i. The following equation may be used to calculate $AS_i$ when the score for the alarm involves a list (e.g., more than one alarm in the case, where $s_i$ may refer to a score for alarm i):

$$AS_i = 1-(1-s_1)\times(1-s_2)\times(1-s_n).$$

Alternatively, fraud score generator component 840 may generate a case score using an equation, such as:

$$CS = \sum_{k=1}^{m} AS_k, \text{ or}$$

$$CS = \sum_{k=1}^{m} AS_k \times AW_k.$$

Fraud score generator component 840 may generate a fraud score for a claim by combining the case scores in some manner. For example, fraud score generator component 840 may generate the fraud score (FS) using an equation, such as:

$$FS = \sum_{k=1}^{n} CS_k.$$

Alternatively, or additionally, each case may have an associated weight value. In this situation, fraud score generator component 840 may generate the fraud score using an equation, such as:

$$FS = \sum_{k=1}^{n} CS_k \times CW_k,$$

where CW may refer to a weight value for a case.

Alert generator component 850 may generate an alert or an alarm and/or a trigger based, for example, on the fraud score. In one implementation, alert generator component 850 may classify the claim, based on the fraud score, into: safe, unsafe, or for review. As described above, fraud detection unit 510 may store policies that indicate, among other things, the thresholds that are to be used to classify a claim as safe, unsafe, or for review. When the claim is classified as safe or unsafe, alert generator component 850 may generate and send the fraud score and/or an alert or alarm (e.g., safe/unsafe or accept/deny) to claims processor 280 so that claims processor 280 can make an intelligent decision as to whether to accept, deny, or fulfill the claim. When the claim is classified as for review, alert generator component 850 may generate and send a trigger to predictive modeling unit 520 so that predictive modeling unit 520 may perform further analysis regarding a claim or a set of claims associated with a case.

Although FIG. 8 shows example functional components of fraud detector component 650, in other implementations, fraud detector component 650 may include fewer functional components, different functional components, differently arranged functional components, and/or additional functional components than those depicted in FIG. 8. Alternatively, or additionally, one or more functional components of fraud detector component 650 may perform one or more tasks described as being performed by one or more other functional components of fraud detector component 650.

Figure 9:
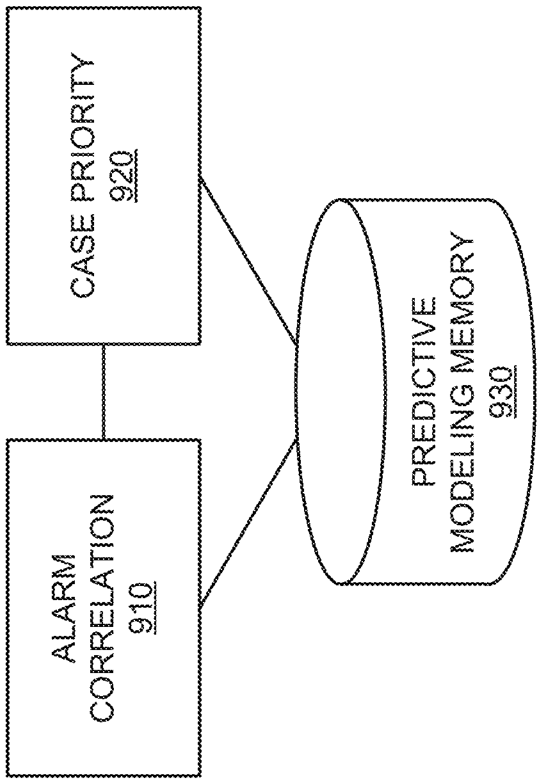
FIG. 9 is a diagram of example functional components of a predictive modeling unit of FIG. 5.

FIG. 9 is a diagram of example functional components of predictive modeling unit 520. In one implementation, the functions described in connection with FIG. 9 may be performed by one or more components of device 300 (FIG. 3) or by one or more devices 300. As shown in FIG. 9, predictive modeling unit 520 may include an alarm correlation component 910, a case priority component 920, and a predictive modeling memory 930.

Alarm correlation component 910 may correlate one or more alerts or alarms (past or present), into groups (called "cases") based on values of one or more of the attributes of the claims associated with the alarms (e.g., provider types, provider names, beneficiary names, etc.). The claims, included in a case, may involve one provider or multiple, unaffiliated providers and/or one beneficiary or multiple, unrelated beneficiaries. In one example, alarm correlation component 910 may correlate one or more alarms into cases based on a particular provider (e.g., as identified by NPI of the provider). In another example, alarm correlation component 910 may correlate one or more alarms into cases based on a particular beneficiary (e.g., as identified by a health insurance contract number (HICN) of the beneficiary). In still another example, alarm correlation component 910 may correlate one or more alarms into cases based on an address (e.g., street, zip code, etc.) associated with a particular provider. Alarm correlation component 910 may correlate one or more alarms across multiple claim types (e.g., a prescription claim, a medical procedure claim, etc.) for trend and link analysis.

In one implementation, alarm correlation component 910 may generate an alarm score for each generated alarm. For example, each alarm may include a value, and alarm correlation component 910 may utilize the value and other parameters to generate a score for each alarm. In one example, each of the claim attributes and/or each of the rules may have a respective associated weight value. Thus, when a particular claim attribute causes a rule to trigger, the generated alarm may have a particular score based on the weight value of the particular claim attribute and/or the weight value of the rule. When a rule involves multiple claims, the generated alarm may have a particular score that is based on a combination of the weight values of the particular claim attributes. In one implementation, alarm correlation component 910 may generate a case score for a case by combining the alarm scores in some manner. For example, alarm correlation component 910 may generate a case score by using a log-based Naïve Bayesian algorithm.

Case priority component 920 may receive alarm scores and/or case scores from alarm correlation component 910, and may prioritize a particular case based on a sum of alarm scores associated with the particular case or based on the case score of the particular case. Case priority component 920 may increase a case score if the claim associated with the case score includes high risk medical procedure codes and/or provider specialties (e.g., physical therapy, psychotherapy, chiropractic procedures, podiatry, ambulance services, pain management services, etc.). Case priority component 920 may increase a case score as the cost of the claim associated with the case score increases. Case priority component 920 may increase a case score if claims associated with the case contain newly-enrolled providers or if suspect geographical locations (e.g., geographically disperse provider and beneficiary) are associated with the case claims.

Predictive modeling memory 930 may include one or more memory devices to store information regarding predictive modeling tools that may be applicable to alarms, alarm scores, case scores, and/or prioritized cases generated by alarm correlation component 910 or case priority component 920. In one implementation, predictive modeling memory 930 may store claim type-specific predictive models, configurable edit rules, artificial intelligence techniques, and/or fraud scores that may be utilized by alarm correlation component 910 and/or case priority component 920 to present a prioritized list of cases for investigation so that claims 410 with the highest risk of fraud may be addressed first. The predictive models stored in predictive modeling memory 930 may support linear pattern recognition techniques (e.g., heuristics, expert rules, etc.) and non-linear pattern recognition techniques (e.g., neural nets, clustering, artificial intelligence, etc.).

Although FIG. 9 shows example functional components of predictive modeling unit 520, in other implementations, predictive modeling unit 520 may include fewer functional components, different functional components, differently arranged functional components, and/or additional functional components than those depicted in FIG. 9. Alternatively, or additionally, one or more functional components of predictive modeling unit 520 may perform one or more tasks described as being performed by one or more other functional components of predictive modeling unit 520.

Figure 10:
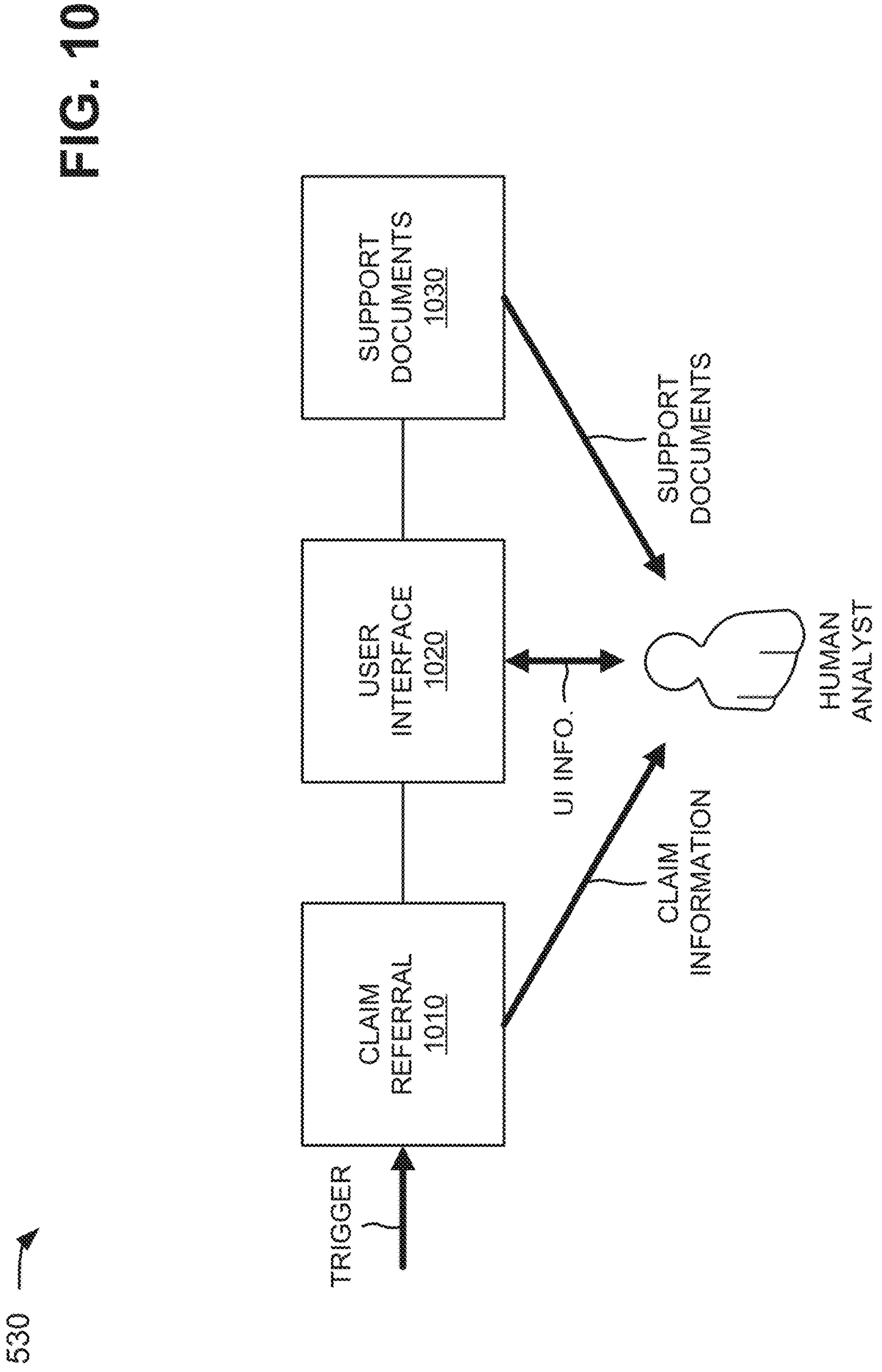
FIG. 10 is a diagram of example functional components of a fraud management unit of FIG. 5.

FIG. 10 is a diagram of example functional components of fraud management unit 530. In one implementation, the functions described in connection with FIG. 10 may be performed by one or more components of device 300 (FIG. 3) or by one or more devices 300. As shown in FIG. 10, fraud management unit 530 may include a claim referral component 1010, a user interface 1020, and a support documents component 1030.

Claim referral component 1010 may receive a trigger from alert generator 850 (FIG. 8) that indicates a particular claim is to be further reviewed for fraud. Based on the trigger, claim referral component 1010 may determine an appropriate human analyst to which to route claim information. In one implementation, claim referral component 1010 may route the claim information (e.g., including alarms, fraud scores, etc.) to a next available human analyst. Alternatively, or additionally, claim referral component 1010 may route the claim information to a human analyst with expertise in handling the particular type of claim. Routing a claim to an appropriate human analyst may improve productivity and streamline healthcare claim processing.

The human analyst may include a person, or a set of people (e.g., licensed clinicians, medical directors, data analysts, certified coders, etc.), trained to research and detect fraudulent claims. The human analyst may analyze "for review" claims (e.g., claims included in consolidated cases) and may perform research to determine whether the claims are fraudulent. Additionally, or alternatively, the human analyst may perform trending analysis, perform feedback analysis, modify existing rules, and/or create new rules. The human analyst may record the results of claim analysis and may present the results to fraud management unit 530 (e.g., via user interface 1020) and/or claims processor 280.

User interface 1020 may include a graphical user interface (GUI) or a non-graphical user interface, such as a text-based interface. User interface 1020 may provide information to users (e.g., human analyst) of healthcare fraud management system 260 via a customized interface (e.g., a proprietary interface) and/or other types of interfaces (e.g., a browser-based interface). User interface 1020 may receive user inputs via one or more input devices, may be user configurable (e.g., a user may change the size of user interface 1020, information displayed in user interface 1020, color schemes used by user interface 1020, positions of text, images, icons, windows, etc., in user interface 1020, etc.), and/or may not be user configurable. User interface 1020 may be displayed to a user via one or more output devices.

In one implementation, user interface 1020 may be a web-based user interface that provides user interface (UI) information associated with healthcare fraud. For example, user interface 1020 may support visual graphic analysis through link analysis and geo-mapping techniques that display relationships between providers and beneficiaries. User interface 1020 may provide a fraud management desktop that displays prioritized cases for near real-time, pre-payment review with integrated workflow and queue management. The fraud management desktop may include a case summary section that lists prioritized cases with supporting aggregated data, and a case detail section that displays alerts and associated events for a selected case. The fraud management desktop may also display map locations for a provider and/or beneficiary associated with a case or claim under review. The human analyst may utilize user interface 1020 to update rule libraries 610 (e.g., thresholds, priority values, etc.) to eliminate or reduce false alarms and to ensure that the highest-risk cases receive immediate attention.

Support documents component 1030 may provide support documents to the human analyst. The support documents may include information such as case activity tracking, notes, external documents, documents that support the medical appeal process and any law enforcement intervention, etc. The support documents may be used by the human analyst to analyze and continuously improve the rules, predictive models, and other techniques used by healthcare fraud management system 260 to identify fraudulent healthcare claims.

In one example implementation, healthcare fraud management system 260 may receive healthcare claims associated with a particular entity, and may select rules for the healthcare claims based on the types of claims, in a manner described above. Healthcare fraud management system 260 may process the healthcare claims using the selected rules, and may collect and sort alarms, generated by the processed healthcare claims, in a manner described above. Healthcare fraud management system 260 may prioritize healthcare information associated with the particular entity in relation to healthcare information associated with other entities, based on the collected and sorted alarms. User interface 1020 may display, to the human analyst, the prioritized healthcare information associated with the particular entity and the other entities. The human analyst may select the displayed healthcare information associated with the particular entity, and user interface 1020 may receive the selection. When selection of the healthcare information associated with the particular entity is received by user interface 1020, information associated with healthcare claims of the particular entity may be displayed by user interface 1020 to the human analyst. Example information that may be displayed by user interface 1020 is described below in connection with FIGS. 11-13.

Although FIG. 10 shows example functional components of fraud management unit 530, in other implementations, fraud management unit 530 may include fewer functional components, different functional components, differently arranged functional components, and/or additional functional components than those depicted in FIG. 10. Alternatively, or additionally, one or more functional components of fraud management unit 530 may perform one or more tasks described as being performed by one or more other functional components of fraud management unit 530.

Figure 11:
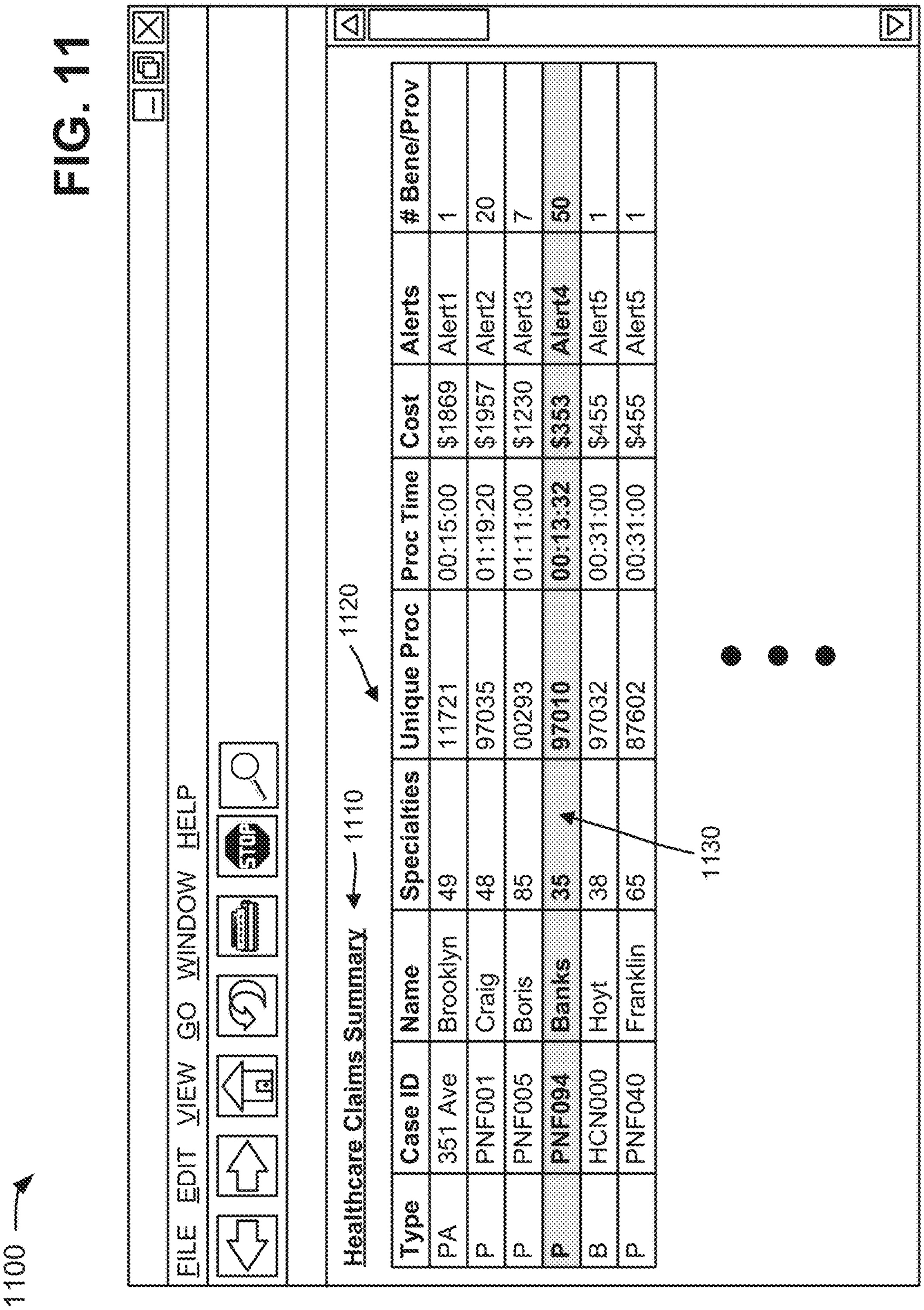
FIG. 11 is a diagram of an example healthcare claims summary user interface that may be generated or provided by the healthcare fraud management system.

FIG. 11 is a diagram of an example healthcare claims summary user interface 1100 that may be generated or provided by healthcare fraud management system 260 (e.g., via user interface 1020, FIG. 10). User interface 1100, as well the user interfaces depicted in FIGS. 12 and 13 (hereinafter referred to as "user interfaces"), may include graphical user interfaces (GUIs) or non-graphical user interfaces, such as text-based interfaces. The user interfaces may provide information to users via customized interfaces (e.g., proprietary interfaces) and/or other types of interfaces (e.g., browser-based interfaces, etc.). The user interfaces may receive user inputs via one or more input devices, may be user-configurable (e.g., a user may change the sizes of the user interfaces, information displayed in the user interfaces, color schemes used by the user interfaces, positions of text, images, icons, windows, etc., in the user interfaces, etc.), and/or may not be user-configurable. Information associated with the user interfaces may be selected and/or manipulated by a user of healthcare fraud management system 260 (e.g., via a touch screen display, a mouse, a keyboard, a keypad, voice commands, etc.).

As shown in FIG. 11, user interface 1100 may include a variety of healthcare information 1110 associated with multiple entities (e.g., beneficiaries, providers, etc.). In one example, healthcare information 1110 may be presented in a prioritized list 1120 so that healthcare claims with the highest risk of fraud may be presented at the top of list 1120. This may enable a user to quickly identify and address the healthcare claims with the highest risk of fraud. Healthcare information 1110 may include, for example, a type field, a case identification (ID) field, a name field, a specialties field, a unique procedure (Proc) field, a procedure time field, a cost field, an alerts field, a number (#) of beneficiaries (Bene) and providers (Prov) field, etc.

The type field may include information associated with a type of entity, such as a provider (P), a beneficiary (B), a provider address (PA), a beneficiary address (BA), etc. The case ID field may include identification information associated with the healthcare claims. For example, the case ID field may include a physical address, alphanumeric characters, a string of letters, numbers, and/or other characters, etc. that may be used to identify a case associated with a particular healthcare claim. The name field may include names, addresses, etc. of entities associated with the healthcare claims.

The specialties field may include healthcare specialty codes (e.g., identifying healthcare specialties, such as general practice, general surgery, dermatology, etc.) associated with the healthcare claims. The unique procedure field may include information (e.g., alphanumeric characters, a string of letters, numbers, and/or other characters, etc.) identifying unique procedures associated with the healthcare claims. The procedure time field may include time periods (e.g., in hours, minutes, and seconds, such as 00:15:00) that it took to perform procedures associated with the healthcare claims. The cost field may include costs (e.g., in dollars) to be paid for the healthcare claims. The alerts field may include alerts associated with the healthcare claims. The number of beneficiaries/providers field may include the numbers of beneficiaries and/or providers associated with the healthcare claims.

A user of healthcare fraud management system 260 (e.g., via user interface 1020, FIG. 10) may select one of the entries provided in prioritized list 1120. For example, the user may select an entry 1130 from prioritized list 1120 via a touch screen display, via a pointer device (e.g., a mouse, etc.), or via another selection mechanism. Entry 1130 may include information associated with healthcare claims of a particular entity (e.g., a provider named Banks). When the user selects entry 1130, user interface 1020 may display another user interface that includes information associated with healthcare claims of the particular entity. An example of such a user interface is described below in connection with FIG. 12.

Although user interface 1100 of FIG. 11 depicts a variety of information, in other implementations, user interface 1100 may depict less information, different information, differently arranged information, and/or additional information than shown in FIG. 11.

FIG. 12 is a diagram of an example user interface 1200, for a particular entity, that may be generated or provided by healthcare fraud management system 260. As shown, user interface 1200 may include information 1210 associated with healthcare claims of a particular entity (e.g., a provider named Barbara Banks). Information 1210 may include a details section 1220, an alerts section 1230, and a claims section 1240.

Details section 1220 may include detailed information associated with the particular entity. For example, details section 1220 may include an identifier (e.g., "PNF094") associated with the particular entity (e.g., "Barbara Banks"), and a priority type associated with the particular entity. The priority type may include a number, or some other designation, identifying a priority type (e.g, high risk, low risk, moderate risk, etc.) associated with the particular entity. Details section 1220 may include a total cost (e.g., "$353.00") of healthcare claims submitted by the particular entity, and unique alerts (e.g., "Alert4") generated by the healthcare claims associated with the particular entity. Details section 1220 may also include information associated with when records of the particular entity were created (e.g., "01/01/2012") and last updated (e.g., "02/01/2012"), and a name (e.g., "Sara") of a user associated with healthcare fraud management system 260.

Details section 1220 may include information associated with specialties (e.g., general practice, general surgery, dermatology, etc.) and case specialties (e.g., specialties associated with particular cases) of the particular entity. Details section 1220 may include information associated with procedures performed by the particular entity, and information associated with procedures of particular cases (e.g., case procedures) performed by the particular entity. Furthermore, details section 1220 may include information associated with beneficiaries served by the particular entity.

Alerts section 1230 may include a variety of information about alerts associated with healthcare claims of the particular entity. Alerts section 1230 may include, for example, a map field, a created field, an updated field, an alert type field, a procedure (Proc) date field, a priority field, a number (#) of procedures field, a number of beneficiaries (Bene) field, a beneficiaries (Benes) field, etc.

The map field may include icons (or some other selection mechanisms) that, when selected, may result in user interface 1020 displaying geographical maps (e.g., such as the geographical map depicted in FIG. 13) associated with the alerts identified in alerts section 1230. The created field may include creation dates associated with the alerts identified in alerts section 1230. The updated field may include dates associated with when the alerts identified in alerts section 1230 are updated. The alert type field may include types (e.g., safe/unsafe or accept/deny) associated with the alerts identified in alerts section 1230. The procedure date field may include dates of procedures for which the alerts, identified in alerts section 1230, are generated. The priority field may include priorities associated with the alerts identified in alerts section 1230. The number of procedures field may include the amounts of the procedures for which the alerts, identified in alerts section 1230, are generated. The number of beneficiaries field may include amounts of beneficiaries associated with the alerts identified in alerts section 1230. The beneficiaries field may include identifiers for the beneficiaries associated with the alerts identified in alerts section 1230.

Claims section 1240 may include a variety of information about healthcare claims associated with the particular entity. Claims section 1240 may include, for example, a type field, a beneficiary identification (ID) field, a perform NPI field, a perform provider identification number (PIN) field, a specialty field, a procedure field, a procedure (Proc) time field, etc. The type field may include information associated with types of entities (e.g., a provider (P), a beneficiary (B), a provider address (PA), a beneficiary address (BA), etc.) associated with the healthcare claims identified in claims section 1240. The beneficiary ID field may include identifiers (e.g., alphanumeric characters, a string of letters, numbers, and/or other characters, etc.) associated with the beneficiaries of the healthcare claims identified in claims section 1240.

The perform NPI field may include a NPI identifier (e.g., alphanumeric characters, a string of letters, numbers, and/or other characters, etc.) associated with the particular entity. The perform PIN field may include a PIN associated with the particular entity. The specialty field may include healthcare specialties (e.g., chiropractic, general practice, general surgery, dermatology, etc.) associated with the healthcare claims identified in claims section 1240. The procedure field may include healthcare procedures (e.g., manual therapy, ultrasound therapy, etc.) associated with the healthcare claims identified in claims section 1240. The procedure time field may include time periods (e.g., in hours, minutes, and seconds, such as 00:15:00) that it took to perform the healthcare procedures identified in the procedures field.

A user of healthcare fraud management system 260 (e.g., via user interface 1020, FIG. 10) may select one of the entries provided in user interface 1200. For example, the user may select a particular icon, provided in the map field of alerts section 1230, via a touch screen display, via a pointer device (e.g., a mouse, etc.), or via another selection mechanism. When the user selects the particular icon, user interface 1020 may display another user interface that includes a geographical map associated with a particular alert of alerts section 1230. An example of such a user interface is described below in connection with FIG. 13.

Although user interface 1200 of FIG. 12 depicts a variety of information, in other implementations, user interface 1200 may depict less information, different information, differently arranged information, and/or additional information than shown in FIG. 12.

Figure 13:
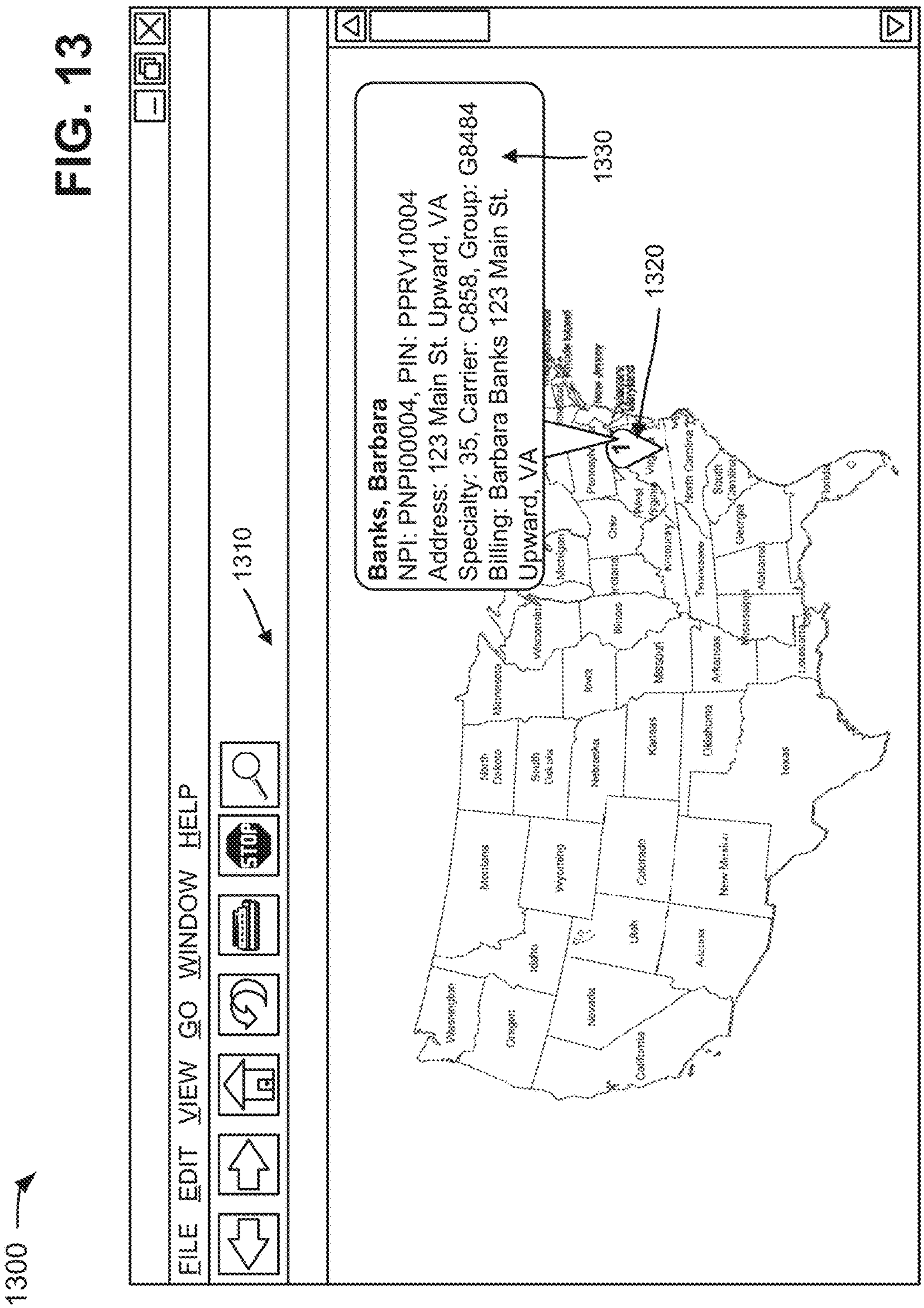
FIG. 13 is a diagram of an example geographical map user interface that may be generated or provided by the healthcare fraud management system.
Figure 14:
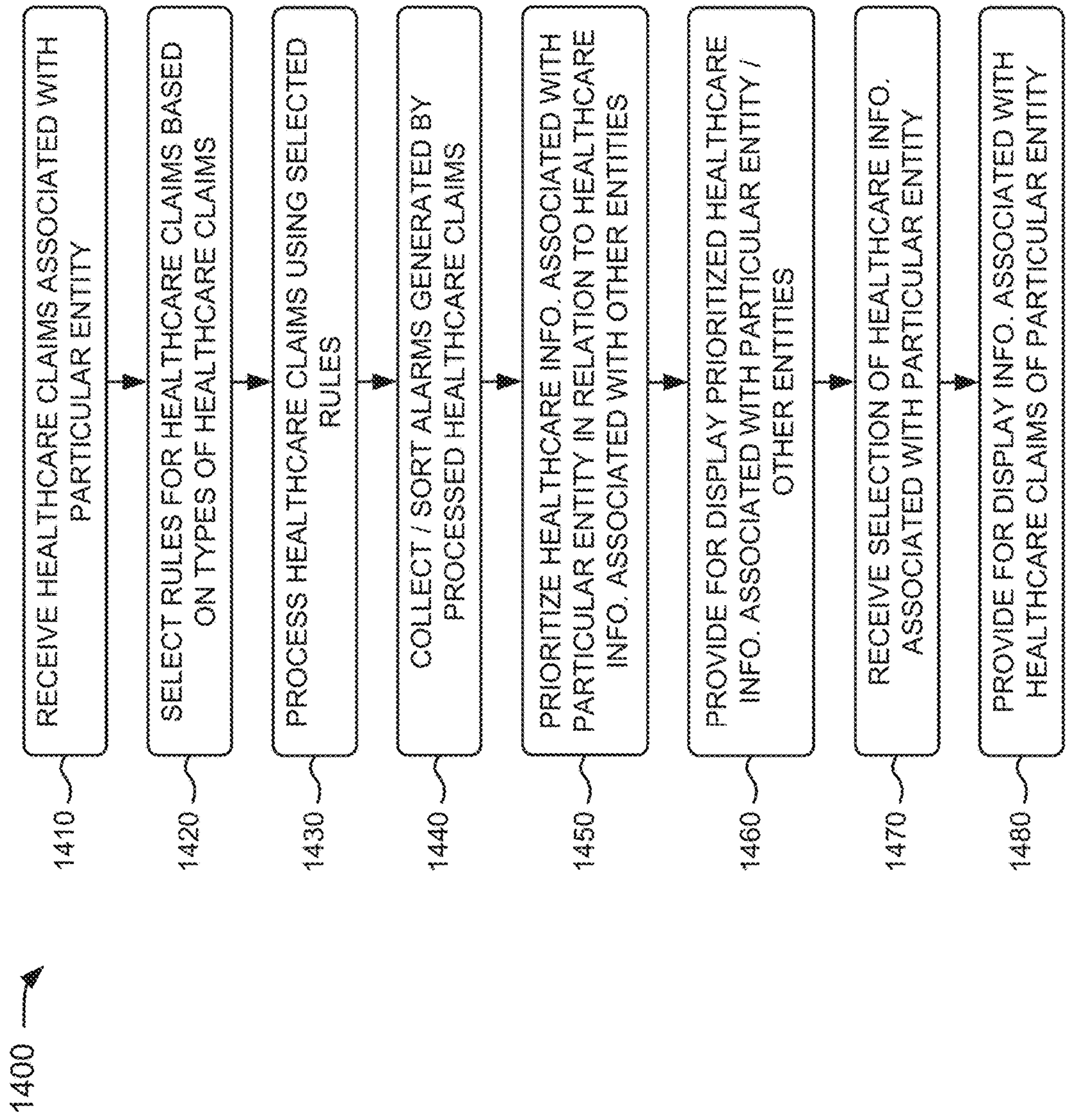
FIGS. 14-17 are flowcharts of an example process for providing case management of healthcare fraud detection information.

FIG. 13 is a diagram of an example geographical map that may be presented in a user interface 1300 that may be generated or provided by healthcare fraud management system 260. As shown, user interface 1300 may include map information 1310 associated with alerts related to the particular entity (e.g., a provider named Barbara Banks), a location indicator 1320, and a details section 1330.

Map information 1310 may include an image of a map of a geographical area serviced by healthcare fraud management system 260. For example, as shown in FIG. 13, map information 1310 may include a geographical map of the continental United States. Alternatively, or additionally, map information 1310 may include a map of another country or countries, a continent, a region of the United States, a particular state (e.g., Virginia), etc.

Location indicator 1320 may provide a mechanism (e.g., an icon, an image, a teardrop, etc.) that identifies a location of an alert related to the particular entity. For example, as shown in FIG. 13, location identifier 1320 may indicate that the alert is located in Virginia. Alternatively, or additionally, multiple location identifiers 1320 may be provided at various locations of the map of the geographical area. The multiple location identifiers 1320 may identify locations of alerts related to the particular entity.

In one example implementation, when a user of healthcare fraud management system 260 selects or hovers over location indicator 1320, details section 1330 may be displayed to the user. Details section 1330 may include details associated with the alert identified by location indicator 1320. For example, as shown in FIG. 13, details section 1330 may include a name (e.g., Barbara Banks) of the particular entity associated with the alert; a NPI identifier (e.g., PNPI00004) associated with the particular entity; a PIN (e.g., PPRV10004) associated with the particular entity; an address (e.g., 123 Main St., Upward, Va.) associated with the particular entity; a specialty code (e.g., "35") associated with the particular entity; a carrier code (e.g., C858) associated with the particular entity; a group code (e.g., G8484) associated with the particular entity; a billing address (e.g., Barbara Banks, 123 Main St., Upward, Va.) associated with the particular entity; etc. Alternatively, or additionally, details section 1330 may include a variety of other information associated with the alert identified by location indicator 1320.

Although user interface 1300 of FIG. 13 depicts a variety of information, in other implementations, user interface 1300 may depict less information, different information, differently arranged information, and/or additional information than shown in FIG. 13.

FIGS. 14-17 are flowcharts of an example process 1400 for providing case management of healthcare fraud detection information. In one implementation, process 1400 may be performed by one or more components/devices of healthcare fraud management system 260. Alternatively, or additionally, one or more blocks of process 1400 may be performed by one or more other components/devices, or a group of components/devices including or excluding healthcare fraud management system 260.

Process 1400 may include receiving healthcare claims associated with a particular entity (block 1410). For example, fraud detector component 650 may receive, from clearinghouse 270, claims involving a provider and a beneficiary. Clearinghouse 270 may use secure communications, such as encryption or a VPN, to send the claims to healthcare fraud management system 260. In one implementation, clearinghouse 270 may send the claims to healthcare fraud management system 260 in near real-time (e.g., after the provider submits the claims to clearinghouse 270) and perhaps prior to payment of the claims. Alternatively, or additionally, clearinghouse 270 may send the claims to healthcare fraud management system 260 after payment of the claims (e.g., after claims processor 280 has provided money to the provider for the claims).

Rules may be selected for the healthcare claims based on types associated with the claims (block 1420). For example, rule selector component 810 may generate a profile for claims based on the claim attributes (e.g., claim type, other information 430, etc.). Based on the claim profile and perhaps relevant information in a white or black list (i.e., information, relevant to the claim, that is present in a white or black list), rule selector component 810 may select a set of libraries 710 within rules memory 630 and/or may select a set of rules within one or more of the selected libraries 710. In one example, rule selector component 810 may select libraries 710, corresponding to general rules, single claim rules, multi-claim rules, provider-specific rules, procedure frequency-specific rules, etc., for claims.

The healthcare claims may be processed using the selected rules (block 1430). For example, fraud detector component 650 may provide the claims to rule engines 720 corresponding to the selected set of libraries 710 for processing. In one implementation, fraud detector component 650 may provide the claims for processing by multiple rule engines 720 in parallel. The claims may also be processed using two or more of the rules, in the selected set of rules of a library 710, in parallel. By processing the claims using select rules, the accuracy of the results may be improved over processing the claims using all of the rules (including rules that are irrelevant to the claims). When a rule triggers (is satisfied), an alarm may be generated. The output of processing the claims using the selected rules may include zero or more alarms.

Alarms generated by the processed healthcare claims may be collected and sorted (block 1440). For example, fraud detector component 650 may aggregate the alarms and may analyze attributes of the claims with which the alarms are associated (e.g., attributes relating to a particular form of payment, a particular geographic area, a particular consumer, etc.). Fraud detector component 650 may correlate the alarms, along with alarms of other claims (past or present associated with the same or different (unaffiliated) providers), into cases based on values of the attributes of the claims associated with alarms. For example, fraud detector component 650 may include one or more alarms associated with a particular beneficiary in a first case, one or more alarms associated with a particular provider location in a second case, one or more alarms associated with a particular medical procedure in a third case, etc. As described above, a particular alarm may be included in multiple cases.

Healthcare information associated with the particular entity and the healthcare claims may be prioritized in relation to healthcare information associated with other entities (block 1450). For example, case priority component 920 may receive alarm scores and/or case scores from alarm correlation component 910, and may prioritize a particular case based on a sum of alarm scores associated with the particular case or based on the case score of the particular case. Case priority component 920 may increase a case score if the claim associated with the case score includes high risk medical procedure codes and/or provider specialties (e.g., physical therapy, psychotherapy, chiropractic procedures, podiatry, ambulance services, pain management services, etc.). Case priority component 920 may increase a case score as the cost of the claim associated with the case score increases. Case priority component 920 may increase a case score if claims associated with the case contain newly-enrolled providers or if suspect geographical locations (e.g., geographically disperse provider and beneficiary) are associated with the case claims.

The prioritized healthcare information associated with the particular entity and the other entities may be provided for display (block 1460). For example, user interface 1100 may include a variety of healthcare information 1110 associated with multiple entities (e.g., beneficiaries, providers, etc.). Healthcare information 1110 may be presented in a prioritized list 1120 so that healthcare claims with the highest risk of fraud may be presented at the top of list 1120. This may enable a user to quickly identify and address the healthcare claims with the highest risk of fraud. Healthcare information 1110 may include, for example, a type field, a case identification (ID) field, a name field, a specialties field, a unique procedure (Proc) field, a procedure time field, a cost field, an alerts field, a number (#) of beneficiaries (Bene) and providers (Prov) field, etc.

Selection of the healthcare information associated with the particular entity may be received (block 1470), and information associated with the healthcare claims of the particular entity may be provided for display (block 1480). For example, a user of healthcare fraud management system 260 (e.g., via user interface 1020, FIG. 10) may select one of the entries provided in prioritized list 1120. In one example, the user may select entry 1130 from prioritized list 1120 via a touch screen display, via a pointer device (e.g., a mouse, etc.), or via another selection mechanism. Entry 1130 may include information associated with healthcare claims of a particular entity (e.g., a provider named Banks). When the user selects entry 1130, user interface 1020 may display another user interface, such as user interface 1200. User interface 1200 may include information 1210 associated with healthcare claims of a particular entity (e.g., a provider named Barbara Banks).

Figure 15:
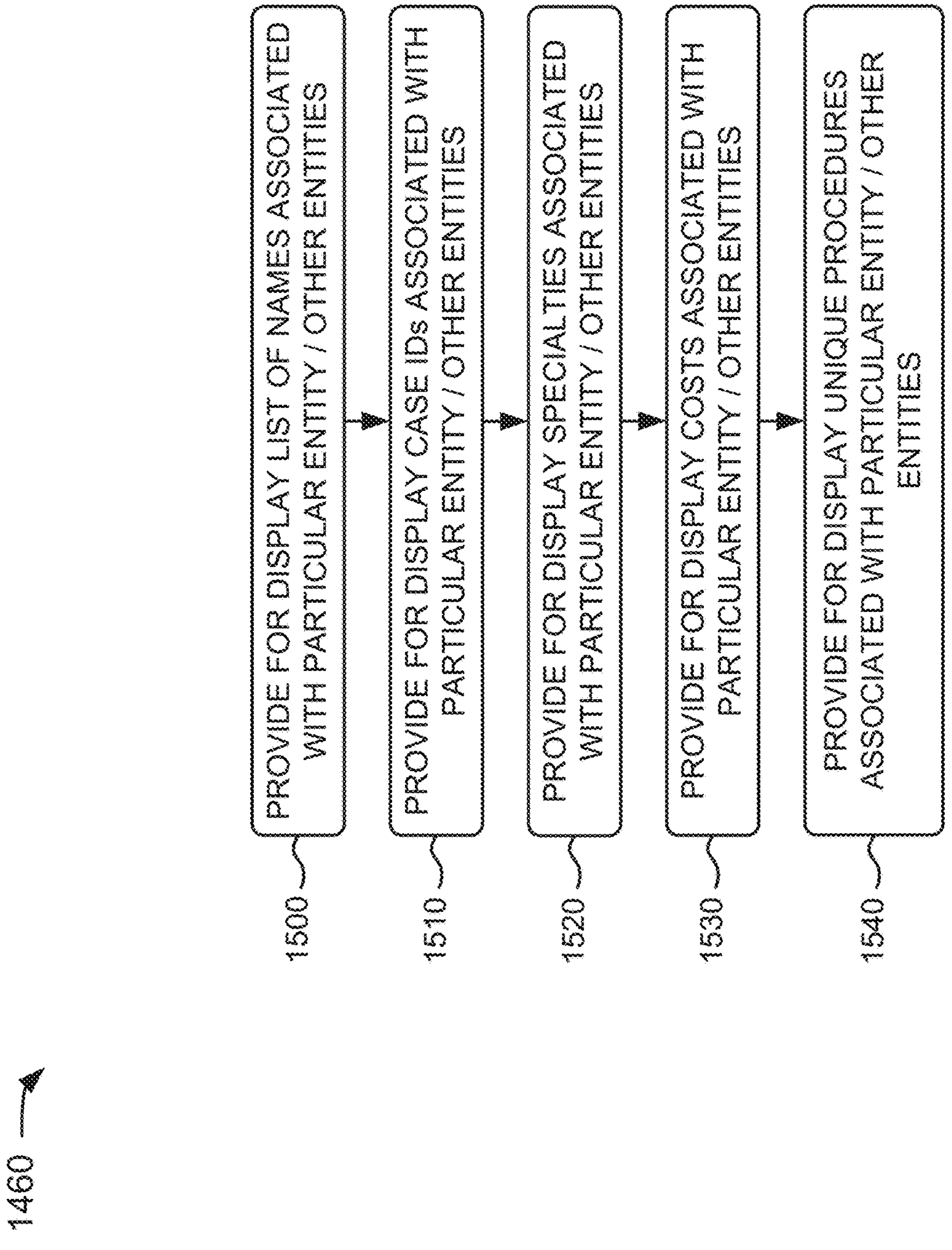

Process block 1460 may include the process blocks depicted in FIG. 15. As shown in FIG. 15, process block 1460 may include providing for display a list of names associated with the particular entity and the other entities (block 1500), and providing for display case IDs associated with the particular entity and the other entities (block 1510). For example, healthcare information 1110 may include a case identification (ID) field and a name field. The case ID field may include identification information associated with the healthcare claims. For example, the case ID field may include a physical address, alphanumeric characters, a string of letters, numbers, and/or other characters, etc. that may be used to identify a case associated with a particular healthcare claim. The name field may include names, addresses, etc. of entities associated with the healthcare claims.

Process block 1460 may also include providing for display specialties associated with the particular entity and the other entities (block 1520), providing for display costs associated with the particular entity and the other entities (block 1530), and providing for display unique procedures associated with the particular entity and the other entities (block 1540). For example, healthcare information 1110 may include a specialties field, a cost field, and a unique procedure field. The specialties field may include healthcare specialty codes (e.g., identifying healthcare specialties, such as general practice, general surgery, dermatology, etc.) associated with the healthcare claims. The cost field may include costs (e.g., in dollars) to be paid for the healthcare claims. The unique procedure field may include information (e.g., alphanumeric characters, a string of letters, numbers, and/or other characters, etc.) identifying unique procedures associated with the healthcare claims.

Figure 16:
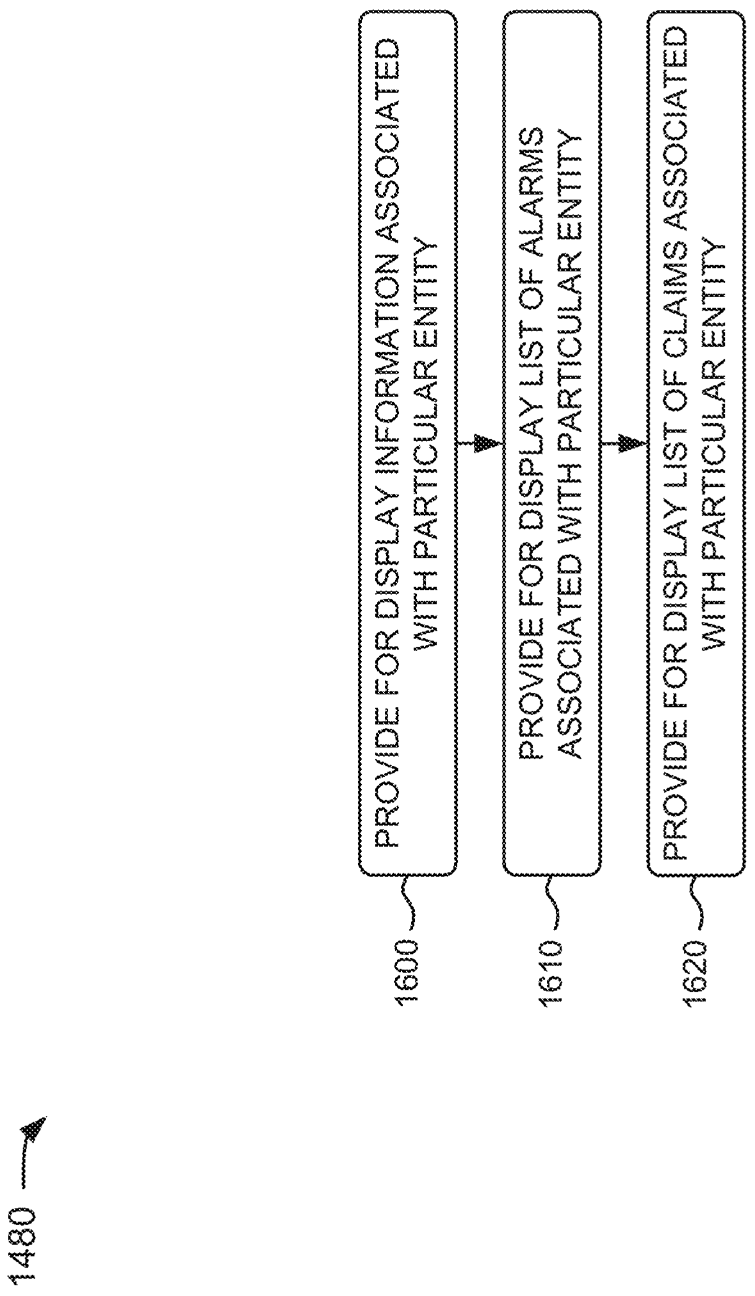

Process block 1480 may include the process blocks depicted in FIG. 16. As shown in FIG. 16, process block 1480 may include providing for display information associated with the particular entity (block 1600), providing for display a list of alarms associated with the particular entity (block 1610), and providing for display a list of claims associated with the particular entity (block 1620). For example, user interface 1200 may include information 1210 associated with healthcare claims of a particular entity (e.g., a provider named Barbara Banks). Information 1210 may include details section 1220, alerts section 1230, and claims section 1240. Details section 1220 may include detailed information associated with the particular entity. Alerts section 1230 may include a variety of information about alerts associated with healthcare claims of the particular entity. Claims section 1240 may include a variety of information about healthcare claims associated with the particular entity.

Figure 17:
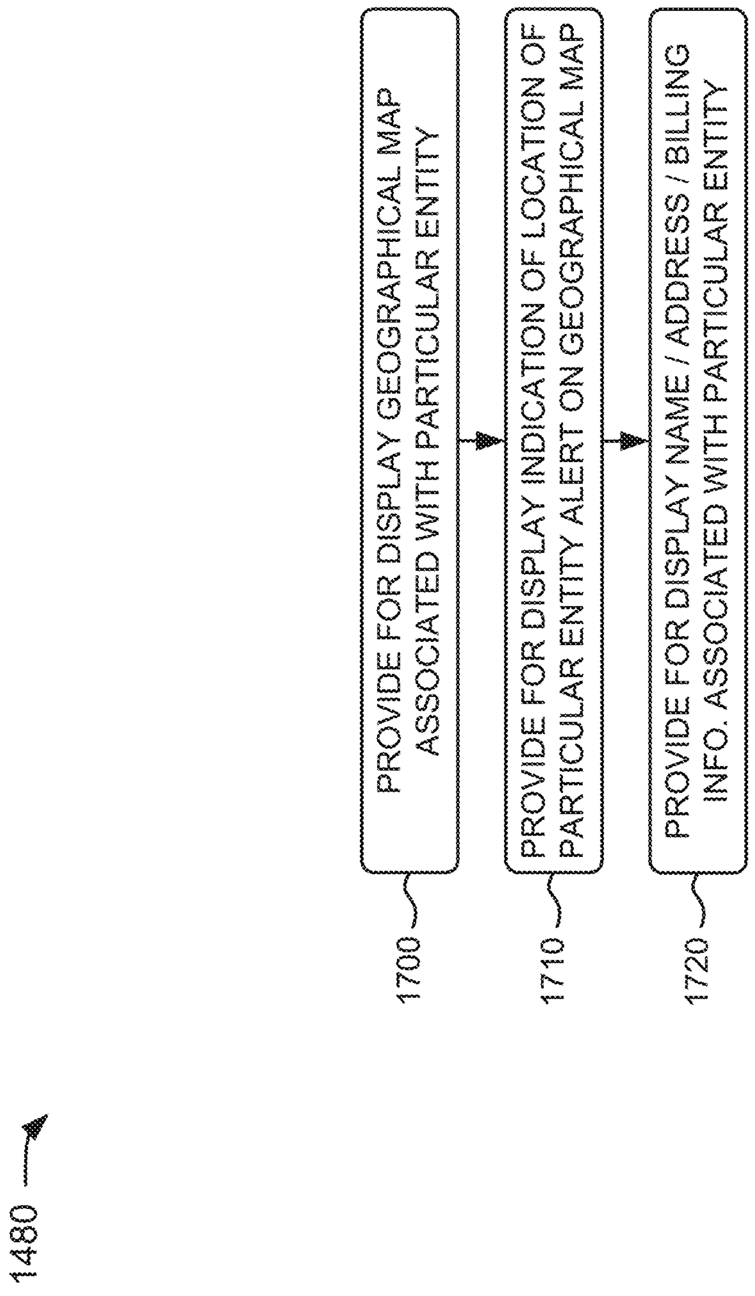

Alternatively, or additionally, process block 1480 may include the process blocks depicted in FIG. 17. As shown in FIG. 17, process block 1480 may include providing for display a geographical map associated with the particular entity (block 1700), providing for display an indication of a location of an alert, associated with the particular entity, on the geographical map (block 1710), and providing for display name, address, and billing information associated with the particular entity (block 1720).

For example, user interface 1300 may include map information 1310 associated with alerts related to the particular entity, location indicator 1320, and details section 1330. Map information 1310 may include an image of a map of a geographical area serviced by healthcare fraud management system 260. Location indicator 1320 may provide a mechanism (e.g., an icon, an image, a teardrop, etc.) that identifies a location of an alert related to the particular entity. When a user of healthcare fraud management system 260 selects or hovers over location indicator 1320, details section 1330 may be displayed to the user. Details section 1330 may include details associated with the alert identified by location indicator 1320. For example, details section 1330 may include a name of the particular entity, an address associated with the particular entity, a specialty code associated with the particular entity, a carrier code associated with the particular entity, a group code associated with the particular entity, etc.

Figure 18:
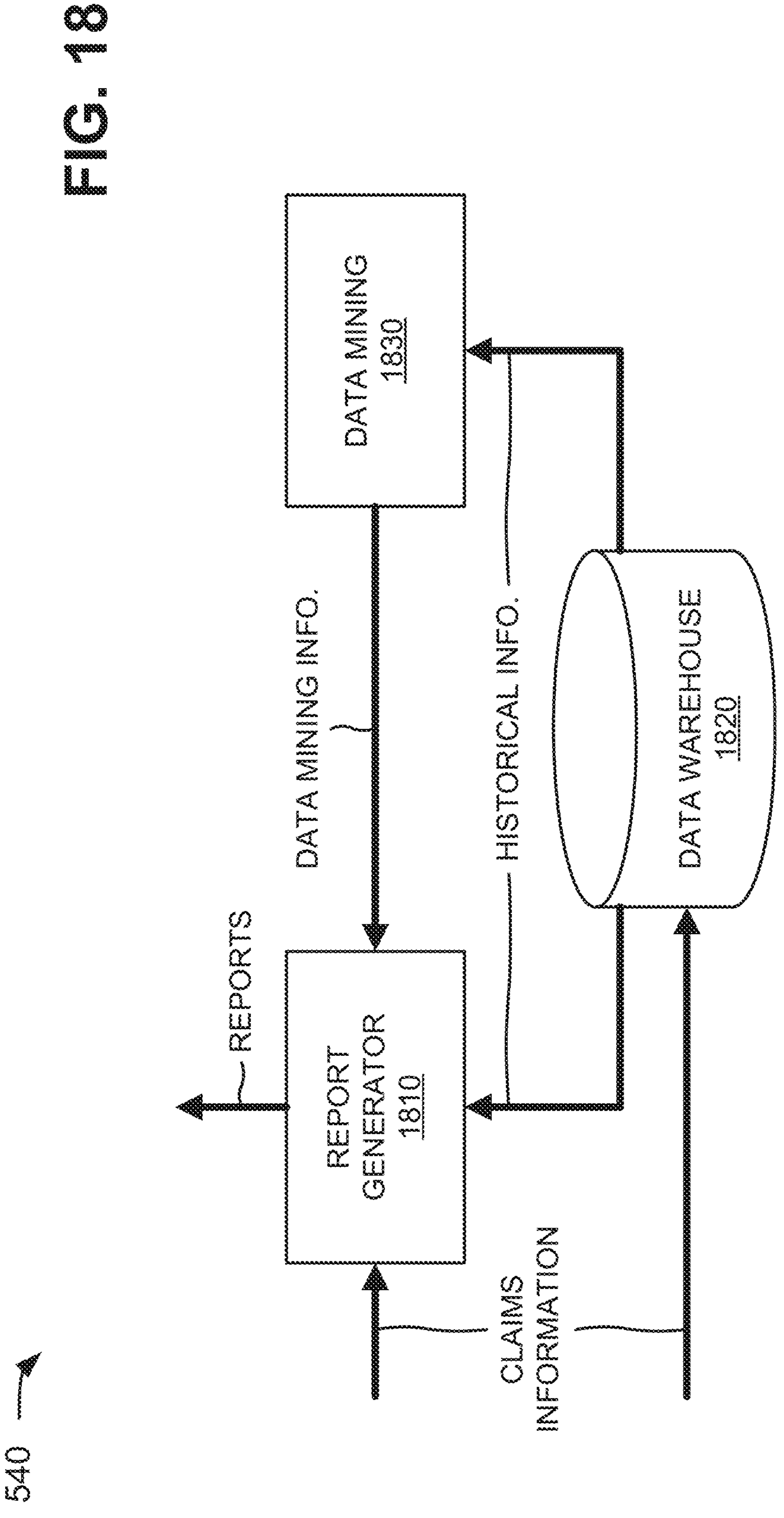
FIG. 18 is a diagram of example functional components of a reporting unit of FIG. 5.

FIG. 18 is a diagram of example functional components of reporting unit 540. In one implementation, the functions described in connection with FIG. 18 may be performed by one or more components of device 300 (FIG. 3) or by one or more devices 300. As shown in FIG. 18, reporting unit 540 may include a report generator component 1810, a data warehouse 1820, and a data mining component 1830.

Report generator component 1810 may receive claims information 420 from clearinghouse 270, may receive historical information from data warehouse 1120, and may receive data mining information from data mining component 1830. The historical information may include historical records of claims from providers, records associated with claims that were processed by a system other than healthcare fraud management system 260, information regarding claims that had been identified as fraudulent, etc. The data mining information may include extracted patterns from the historical information. Report generator 1810 may generate regular operational and management reports, weekly reports with a list of high priority suspect cases, etc. based on claims information 420, the historical information, and/or the data mining information. The regular operational and management reports may include financial management reports, trend analytics reports, return on investment reports, KPI/performance metrics reports, intervention analysis/effectiveness report, etc.

Data warehouse 1820 may include one or more memory devices to store the claims information (e.g., claims information 420) and the historical information. Information provided in data warehouse 1820 may include alerts and case management data associated with healthcare claims. Such information may be available to claims analysts for trending, post data analysis, and additional claims development, such as preparing a claim for submission to PSCs and other authorized entities.

Data mining component 1830 may receive the historical information from data warehouse 1820 and may perform data mining techniques on the historical information. The data mining techniques may include clustering, classification, regression, and association rule learning. Clustering may include discovering groups and structures in the data that are in some way or another similar, without using known structures in the data. Classification may include generalizing a known structure to apply to new data (e.g., using decision tree learning, nearest neighbor, log-based Naïve Bayesian classification, neural networks, and support vector machines). Regression may include attempting to locate a function that models the data with the least error. Association rule learning may include searches for relationships between variables. Based on the data mining techniques, data mining component 1830 may generate the data mining information that is provided to report generator component 1810.

Although FIG. 18 shows example functional components of reporting unit 540, in other implementations, reporting unit 540 may include fewer functional components, different functional components, differently arranged functional components, and/or additional functional components than those depicted in FIG. 18. Alternatively, or additionally, one or more functional components of reporting unit 540 may perform one or more tasks described as being performed by one or more other functional components of reporting unit 540.

Figure 19:
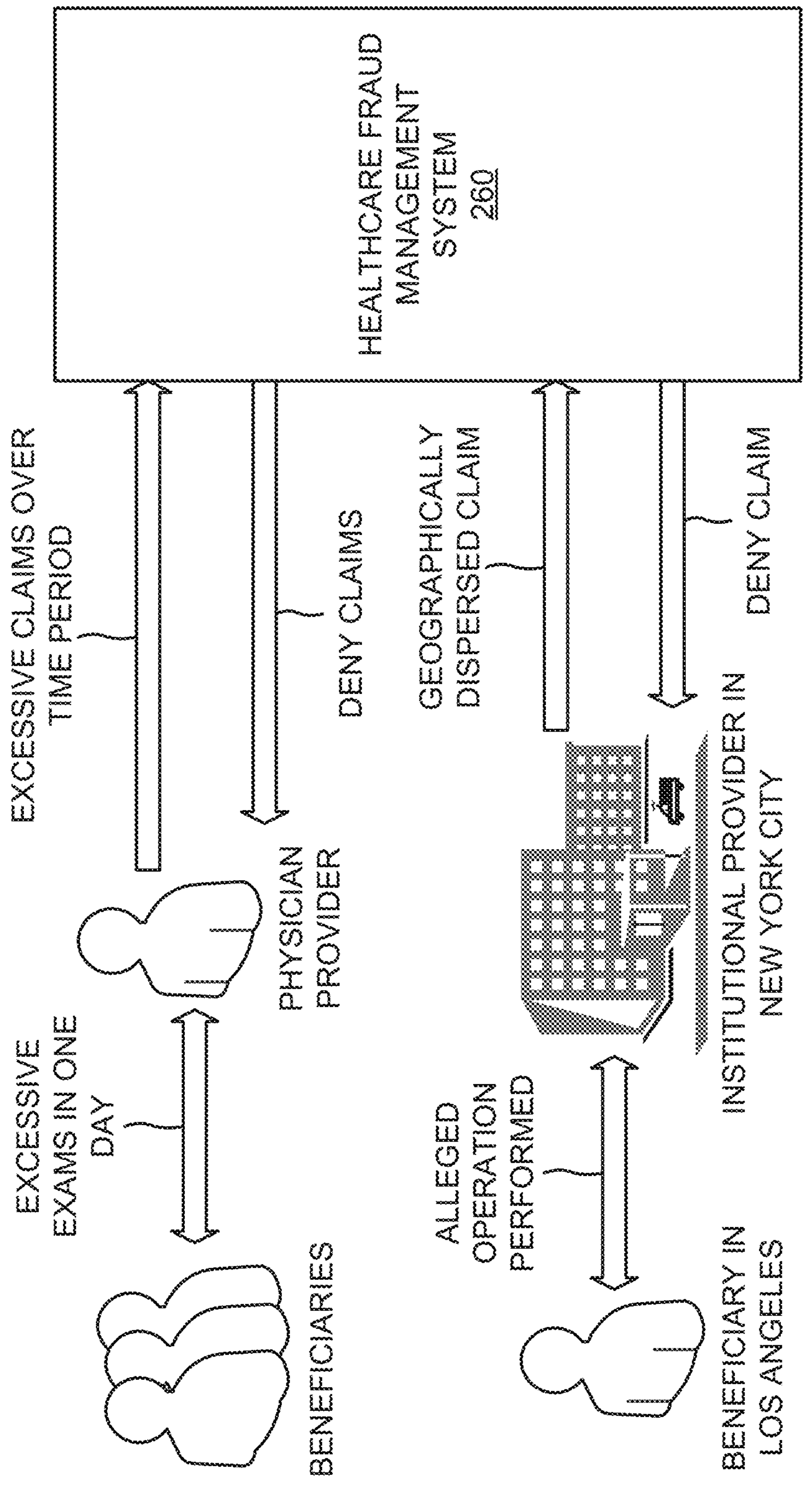
FIG. 19 is a diagram illustrating an example for identifying a fraudulent healthcare claim.

FIG. 19 is a diagram illustrating an example for identifying a fraudulent healthcare claim. As shown in FIG. 19, a physician provider may perform an excessive number of examinations in one day for beneficiaries. For example, the physician provider may allegedly perform thirty (30) hours of examinations in a single day. The physician provider may submit, to healthcare fraud management system 260, an excessive number of claims that correspond to the excessive number of examinations performed in a time period (e.g., one day). Healthcare fraud management system 260 may receive the excessive claims, and may process the excessive claims. For example, healthcare fraud management system 260 may obtain other information 430 relevant to the excessive claims, may select rules for the claims, such as beneficiary frequency-specific rules, and may process the claims using the selected rules. Assume that a set of the selected rules trigger and generate corresponding alarms. For example, one rule may generate an alarm because the physician provider has treated an excessive number of beneficiaries in a particular time period.

Healthcare fraud management system 260 may process the alarms and determine, for example, that the excessive claims are potentially fraudulent based on the information known to healthcare fraud management system 260. Healthcare fraud management system 260 may notify clearinghouse 270 or claims processor 280 (not shown) that the excessive claims are potentially fraudulent, and may instruct clearinghouse 270 or claims processor 280 to deny the excessive claims.

As further shown in FIG. 19, a beneficiary located in Los Angeles, Calif. may have a procedure performed in Los Angeles, and may have an operation performed by an institutional provider located in New York City, N.Y. on the same day. The institutional provider may submit, to healthcare fraud management system 260, a geographically dispersed claim that corresponds to the alleged operation performed for the remotely located beneficiary. Healthcare fraud management system 260 may receive the geographically dispersed claim, and may process the geographically dispersed claim. For example, healthcare fraud management system 260 may obtain other information 430 relevant to the geographically dispersed claim, may select rules for the claims, such as geographical dispersion of services-specific rules, and may process the claim using the selected rules. Assume that a set of the selected rules trigger and generate corresponding alarms. For example, one rule may generate an alarm because the beneficiary in Los Angeles receives a service from the Los Angeles provider and from the New York City provider on the same day. In other words, it may be highly unlikely that person living in Los Angeles would have procedures done in Los Angeles and in New York City on the same day.

Healthcare fraud management system 260 may process the alarms and determine, for example, that the geographically dispersed claim is potentially fraudulent based on the information known to healthcare fraud management system 260. Healthcare fraud management system 260 may notify clearinghouse 270 or claims processor 280 (not shown) that the geographically dispersed claim is potentially fraudulent, and may instruct clearinghouse 270 or claims processor 280 to deny the geographically dispersed claim.

The foregoing description provides illustration and description, but is not intended to be exhaustive or to limit the invention to the precise form disclosed. Modifications and variations are possible in light of the above disclosure or may be acquired from practice of the invention.

For example, while a series of blocks have been described with regard to FIGS. 14-17, the order of the blocks may be modified in other implementations. Further, non-dependent blocks may be performed in parallel.

It will be apparent that different aspects of the description provided above may be implemented in many different forms of software, firmware, and hardware in the implementations illustrated in the figures. The actual software code or specialized control hardware used to implement these aspects is not limiting of the invention. Thus, the operation and behavior of these aspects were described without reference to the specific software code—it being understood that software and control hardware can be designed to implement these aspects based on the description herein.

Even though particular combinations of features are recited in the claims and/or disclosed in the specification, these combinations are not intended to limit the disclosure of the invention. In fact, many of these features may be combined in ways not specifically recited in the claims and/or disclosed in the specification. Although each dependent claim listed below may directly depend on only one other claim, the disclosure of the invention includes each dependent claim in combination with every other claim in the claim set.

No element, act, or instruction used in the present application should be construed as critical or essential to the invention unless explicitly described as such. Also, as used herein, the article “a” is intended to include one or more items and may be used interchangeably with ‘one or more. Where only one item is intended, the term “one” or similar language is used. Further, the phrase “based on” is intended to mean “based, at least in part, on” unless explicitly stated otherwise.

What is claimed is:

1. A method, comprising:

receiving, by one or more computer devices of a healthcare fraud management system, a first plurality of healthcare claims;

applying, by the one or more computer devices and in real time or near real time, a plurality of rules to the first plurality of healthcare claims;

generating, by the one or more computer devices and in real time or near real time, a plurality of alarms based on applying the plurality of rules to the first plurality of healthcare claims, a first alarm, of the plurality of alarms, being generated based on a first healthcare claim, of the first plurality of healthcare claims, and a second healthcare claim, of the first plurality of healthcare claims, that satisfy at least one rule of the plurality of rules, the second healthcare claim being different from the first healthcare claim, a second alarm, of the plurality of alarms, being generated based on a third healthcare claim, of the first plurality of healthcare claims, that satisfies at least one other rule of the plurality of rules, the second alarm being different from the first alarm, the third healthcare claim being different from the first healthcare claim and the second healthcare claim, a third alarm, of the plurality of alarms, being generated based on at least one of the first healthcare claim, the second healthcare claim, or the third healthcare claim, the third alarm being different from the first alarm and the second alarm;

forming, by the one or more computer devices, a first case, associated with the first healthcare claim, by combining the first alarm and the second alarm based on an attribute of two or more of the first healthcare claim, the second healthcare claim, or the third healthcare claim;

determining, by the one or more computer devices and in real time or near real time, a first case score associated with the first case;

forming, by the one or more computer devices and in real time or near real time, a second case, associated with the first healthcare claim, based on the third alarm;

determining, by the one or more computer devices and in real time or near real time, a second case score associated with the second case;

determining, by the one or more computer devices and in real time or near real time, a fraud score, associated with the first healthcare claim, based on the first case score and the second case score;

selectively applying, by the one or more computer devices and in real time or near real time, predictive modeling to information associated with the first healthcare claim to determine whether the first healthcare claim is fraudulent, the predictive modeling being selectively applied based on whether the fraud score satisfies a threshold score, and when the predictive modeling is applied, applying the predictive modeling including using a streaming data reduction platform to normalize and filter the information associated with the first healthcare claim to reduce the information associated with the first healthcare claim to a size that may be processed in real time or near real time;

providing, by the one or more computer devices and based on selectively applying the predictive modeling, an indication associated with the first healthcare claim, the indication associated with the first healthcare claim being provided in real time or near real time to a claims processor device, and causing at least one of:

acceptance of the first healthcare claim prior to payment of the first healthcare claim by the claims processor device, or denial of the first healthcare claim prior to payment of the first healthcare claim by the claims processor device;

receiving, by the one or more computer devices and in real time or near real time, a second set of one or more healthcare claims;

selectively applying, by the one or more computer devices and in real time or near real time, the predictive modeling to information associated with the second set of one or more healthcare claims to determine whether the first healthcare claim is fraudulent; and updating, by the one or more computer devices, based on selectively applying the predictive modeling to the information associated with the second set of one or more healthcare claims, and in real time or near real time, the indication associated with the first healthcare claim.

2. The method of claim 1, where the information associated with the first healthcare claim includes one or more of:

a name associated with the first healthcare claim, a case identification associated with the first healthcare claim, a specialty associated with the first healthcare claim, a cost associated with the first healthcare claim, or a procedure associated with the first healthcare claim.

3. The method of claim 1, where the information associated with the first healthcare claim includes:

information that identifies a geographical map, and an indication of a location of an alarm associated with the first healthcare claim, the indication of the location being provided for display on the geographical map.

4. The method of claim 1, where the plurality of rules includes at least one of:

provider-specific rules;

provider type-specific rules;

beneficiary-specific rules;

procedure frequency-specific rules;

geographical dispersion of services-specific rules;

single claim analysis-related rules;

auto summation of provider procedure time-specific rules;

suspect beneficiary ID theft-specific rules;

alert on suspect address-specific rules;

inconsistent relationship-specific rules;

excessive cost-specific rules;

rules that identify fraudulent therapies; or rules that identify a gang visit fraud scheme where a provider bills as if services have been provided to all beneficiaries in a facility.

5. The method of claim 1, where providing the indication associated with the first healthcare claim comprises:

providing the indication associated with the first healthcare claim to the claims processor device in real-time or near real-time.

6. The method of claim 1, further comprising:

generating a plurality of fraud scores corresponding to the first plurality of healthcare claims, the plurality of fraud scores including the fraud score;

generating a prioritized list of the first plurality of healthcare claims based on the plurality of fraud scores; and providing the prioritized list of the first plurality of healthcare claims.

7. The method of claim 1, where forming the second case comprises:

forming the second case based on the first alarm or the second alarm.

8. A system, comprising:

one or more memory devices to store a plurality of rules for detecting fraud; and one or more processors to:

receive a first plurality of claims;

apply, in real time or near real time, the plurality of rules to the first plurality of claims based on receiving the first plurality of claims;

generate, in real time or near real time, a plurality of alarms based on applying the plurality of rules to the first plurality of claims, the plurality of alarms being generated based on a fraud detector unit transmitting the first plurality of claims to a rules engine, the rules engine applying the plurality of rules to the first plurality of claims, and the rules engine generating, based on applying the plurality of rules, the plurality of alarms, a first alarm, of the plurality of alarms, being generated based on a first claim, of the first plurality of claims, and a second claim, of the first plurality of claims, that satisfy at least one rule of the plurality of rules, the second claim being different from the first claim, a second alarm, of the plurality of alarms, being generated based on a third claim, of the first plurality of claims, that satisfies at least one other rule of the plurality of rules, the second alarm being different from the first alarm, the third claim being different from the first claim and the second claim, a third alarm, of the plurality of alarms, being generated based on at least one of the first claim, the second claim, or the third claim, the third alarm being different from the first alarm and the second alarm;

form, in real time or near real time, a first case, associated with the first claim, by combining the first alarm and the second alarm based on an attribute of two or more of the first claim, the second claim, or the third claim, the first case being formed by an alarm combiner and analyzer unit receiving the first alarm and the second alarm, analyzing the attribute, and forming the first case based on the analyzed attribute;

determine, in real time or near real time, a first case score associated with the first case, the first case score being determined based on a fraud score generator unit receiving, from the alarm combiner and analyzer unit, information associated with the first case, analyzing the information associated with the first case, and determining the first case score based on analyzing the information associated with the first case;

form, in real time or near real time, a second case, associated with the first claim, based on the third alarm, the second case being formed by the alarm combiner and analyzer unit receiving the third alarm, analyzing an attribute associated with the third alarm, and forming the second case based on the analyzed attribute associated with the third alarm;

determine, in real time or near real time, a second case score associated with the second case, the second case score being determined based on the fraud score generator unit receiving, from the alarm combiner and analyzer unit, information associated with the second case, analyzing the information associated with the second case, and determining the second case score based on analyzing the information associated with the second case;

determine, in real time or near real time, a fraud score, for the first claim, based on the first case score and the second case score;

selectively apply, in real time or near real time, predictive modeling to information associated with the first claim to determine whether the first claim is fraudulent, the predictive modeling being selectively applied based on whether the fraud score satisfies a threshold score, and when the predictive modeling is applied, applying the predictive modeling including using a streaming data reduction platform to normalize and filter the information associated with the first claim to reduce the information associated with the first claim to a size that may be processed in real time or near real time;

provide, based on selectively applying the predictive modeling, an indication associated with the first claim, the indication associated with the first claim being provided in real time or near real time to a claims processor device, and causing at least one of:

acceptance of the first claim prior to payment of the first claim by the claims processor device, or denial of the first claim prior to payment of the first claim by the claims processor device;

receive, in real time or near real time, a second set of one or more claims;

selectively apply, in real time or near real time, the predictive modeling to information associated with the second set of one or more claims to determine whether the first claim is fraudulent; and update, based on selectively applying the predictive modeling to the information associated with the second set of one or more claims and in real time or near real time, the indication associated with the first claim.

9. The system of claim 8, where the information associated with the first claim includes a list of alarms associated with the first claim.

10. The system of claim 8, where the information associated with the first claim includes:

information that identifies a geographical map associated with the first claim; and an indication, provided in association with the geographical map, of a location associated with at least one of:

the first alarm, the second alarm, or the third alarm.

11. The system of claim 8, where the plurality of rules includes at least one of:

provider-specific rules;

provider type-specific rules;

beneficiary-specific rules;

procedure frequency-specific rules;

geographical dispersion of services-specific rules;

single claim analysis-related rules;

auto summation of provider procedure time-specific rules;

suspect beneficiary ID theft-specific rules;

alert on suspect address-specific rules;

inconsistent relationship-specific rules;

excessive cost-specific rules;

rules that identify fraudulent therapies; or rules that identify a gang visit fraud scheme where a provider bills as if services have been provided to all beneficiaries in a facility.

12. The system of claim 8, where the indication associated with the first claim is provided to the claims processor device to accept or deny the first claim.

13. The system of claim 8, where the one or more processors are further to:

generate a plurality of fraud scores corresponding to the plurality of claims, the plurality of fraud scores including the fraud score;

generate a prioritized list of the plurality of claims based on the plurality of fraud scores; and provide the prioritized list.

14. The system of claim 8, where the one or more processors, when forming the second case, are to:

form the second case based on the first alarm.

15. A non-transitory computer-readable medium storing instructions, the instructions comprising:

one or more instructions that, when executed by one or more processors, cause the one or more processors to:

receive a first plurality of claims;

apply, in real time or near real time, a plurality of rules to the first plurality of claims based on receiving the first plurality of claims;

generate, in real time or near real time, a plurality of alarms based on applying the plurality of rules to the first plurality of claims, the plurality of alarms being generated based on a fraud detector unit transmitting the first plurality of claims to a rules engine, the rules engine applying the plurality of rules to the first plurality of claims, and the rules engine generating, based on applying the plurality of rules, the plurality of alarms, a first alarm, of the plurality of alarms, being generated based on a first claim, of the first plurality of claims, and a second claim, of the first plurality of claims, that satisfy at least one rule of the plurality of rules, the second claim being different from the first claim, a second alarm, of the plurality of alarms, being generated based on a third claim, of the first plurality of claims, that satisfies at least one other rule of the plurality of rules, the second alarm being different from the first alarm, the third claim being different from the first claim and the second claim, a third alarm, of the plurality of alarms, being generated based on at least one of the first claim, the second claim, or the third claim, the third alarm being different from the first alarm and the second alarm;

form, in real time or near real time, a first case, associated with the first claim, by combining the first alarm and the second alarm based on an attribute of two or more of the first claim, the second claim, or the third claim, the first case being formed by an alarm combiner and analyzer unit receiving the first alarm and the second alarm, analyzing the attribute, and forming the first case based on the analyzed attribute;

determine, in real time or near real time, a first case score associated with the first case, the first case score being determined based on a fraud score generator unit receiving, from the alarm combiner and analyzer unit, information associated with the first case, analyzing the information associated with the first case, and determining the first case score based on analyzing the information associated with the first case;

form, in real time or near real time, a second case, associated with the first claim, based on the third alarm, the second case being formed by the alarm combiner and analyzer unit receiving the third alarm, analyzing an attribute associated with the third alarm, and forming the second case based on the analyzed attribute associated with the third alarm;

determine, in real time or near real time, a second case score associated with the second case, the second case score being determined based on the fraud score generator unit receiving, from the alarm combiner and analyzer unit, information associated with the second case, analyzing the information associated with the second case, and determining the second case score based on analyzing the information associated with the second case;

determine, in real time or near real time, a fraud score, for the first claim, based on the first case score and the second case score;

selectively apply, in real time or near real time, predictive modeling to information associated with the first claim to determine whether the first claim is fraudulent, the predictive modeling being selectively applied based on whether the fraud score satisfies a threshold score, and when the predictive modeling is applied, applying the predictive modeling including using a streaming data reduction platform to normalize and filter the information associated with the first claim to reduce the information associated with the first claim to a size that may be processed in real time or near real time; and provide, based on selectively applying the predictive modeling, an indication associated with the first claim, the indication associated with the first claim being provided in real time or near real time to a claims processor device, and causing at least one of:

acceptance of the first claim prior to payment of the first claim by the claims processor device, or denial of the first claim prior to payment of the first claim by the claims processor device;

receive, in real time or near real time, a second set of one or more claims;

selectively apply, in real time or near real time, the predictive modeling to information associated with the second set of one or more claims to determine whether the first claim is fraudulent; and update, based on selectively applying the predictive modeling to the information associated with the second set of one or more claims, and in real time or near real time, the indication associated with the first claim.

16. The non-transitory computer-readable medium of claim 15, where the information associated with the first claim includes:

information that identifies the first alarm, the second alarm, or the third alarm.

17. The non-transitory computer-readable medium of claim 15, where the information associated with the first claim includes:

information that identifies a geographical map associated with the first claim, and an indication of a location, represented on the geographical map, of an alarm associated with the first claim.

18. The non-transitory computer readable medium of claim 15, where the one or more instructions, when executed by the one or more processors, further cause the one or more processors to:

generate a plurality of fraud scores corresponding to the plurality of claims, the plurality of fraud scores including the fraud score;

generate a prioritized list of the plurality of claims based on the plurality of fraud scores; and provide the prioritized list for display.

19. The non-transitory computer readable medium of claim 15, where the one or more instructions, that cause the one or more processors to form the second case, cause the one or more processors to:

form the second case based on the second alarm.

20. The non-transitory computer readable medium of claim 15, where the plurality of rules includes at least one of:

provider-specific rules;

provider type-specific rules;

beneficiary-specific rules;

procedure frequency-specific rules;

geographical dispersion of services-specific rules;

single claim analysis-related rules;

auto summation of provider procedure time-specific rules;

suspect beneficiary ID theft-specific rules;
alert on suspect address-specific rules;
inconsistent relationship-specific rules;
excessive cost-specific rules;
rules that identify fraudulent therapies; or
rules that identify a gang visit fraud scheme where a provider bills as if services have been provided to all beneficiaries in a facility.

* * * * *